US008595672B2

(12) United States Patent
Herbst

(10) Patent No.: US 8,595,672 B2
(45) Date of Patent: *Nov. 26, 2013

(54) METHOD AND APPARATUS FOR CONFIGURABLE SYSTEMS

(75) Inventor: Ewa Herbst, Edgewater, NJ (US)

(73) Assignee: Innovations Holdings, L.L.C., Edgewater, NJ (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/152,242

(22) Filed: Jun. 2, 2011

(65) Prior Publication Data

US 2012/0204132 A1 Aug. 9, 2012

Related U.S. Application Data

(63) Continuation of application No. PCT/US2009/066463, filed on Dec. 2, 2009, which is a continuation-in-part of application No. 13/085,366, filed on Apr. 12, 2011, now Pat. No. 8,365,122, which is a continuation of application No. 12/113,200, filed on Apr. 30, 2008, now Pat. No. 7,937,683, which is a continuation-in-part of application No. 12/485,855, filed on Jun. 16, 2009, now abandoned.

(60) Provisional application No. 61/119,244, filed on Dec. 2, 2008, provisional application No. 60/926,954, filed on Apr. 30, 2007, provisional application No. 61/129,285, filed on Jun. 16, 2008.

(51) Int. Cl.
*G06F 17/50* (2006.01)

(52) U.S. Cl.
USPC ............ 716/116; 716/117; 716/138; 716/139

(58) Field of Classification Search
USPC ................. 716/100–104, 116–117, 121, 128, 716/138–139
See application file for complete search history.

(56) References Cited

U.S. PATENT DOCUMENTS

2009/0037863 A1* 2/2009 Breyer et al. ................... 716/11

* cited by examiner

*Primary Examiner* — Paul Dinh
(74) *Attorney, Agent, or Firm* — Byrne Poh LLP

(57) ABSTRACT

The invention relates to methods and devices to define and control the design of a configurable chip module, instrument or systems, for example, for measurement, control and communication systems or any portion thereof. The module may include one or more chip elements. This can be achieved using, for example, a Graphical User interface (GUI), that transforms selections made by the user to a hardware and/or software configuration for the system in a process transparent to the user. This enables implementation of a plurality of devices and larger subsystems on a chip or chip module without specific semiconductor design knowledge from the user. This transformation process is thus accomplished transparently to the user, who operates the GUI to define the measurement or action which needs to be performed thereby resulting in an automatic combination of hardware and/or software elements available to create a specific configuration.

29 Claims, 35 Drawing Sheets

- High Impedance Amplifier
  - Probe Types (High Impedance)
    - Ion Selective Electrode: H+ (pH), Ca++, K+, Na+, Li+, CO₃²⁻, Cl⁻, NH₄⁺
    - Conductivity, Dissolved Oxygen
    - Glucose
    - Blood Gases
  - Specialty: Input resistance >10¹⁵ Ω

Apps: Electrochemical

- Differential Amplifier
  - Probes:
    - Thermocouple, RTD, Thermistor
    - Electrodes
  - Specialty: CJC compensation, Temperature control

- BioAmplifier
  - Electrodes: EMG, EKG, EEG
  - Biopotential Electrode
  - Electrodes: Cell potential
  - Specialty: Selectable Notch, Low Pass, High Pass Filtering with Differential and Isolation Amps, some provide excitation

- Wheatstone Bridge Amplifier
  - Probes Types
    - Strain Gauge
    - Displacement Transducer
    - Pressure/ differential pressure Transducer
      - Air Flow, O₂ Flow, BP
    - Temperature Transducer
    - Glucose
  - Specialty: Provide controlled AC/DC Excitation
  - Measurements: Blood Pressure, Glucose.

- Transimpedance Amplifier
  - Probes Types
    - Optical: Photodiodes, pH, Phosphorescence
    - Fluorescence
    - Radioactive
    - Current to voltage
  - Specialty: Provides excitation light
  - Glucose, pH.

Fig. 7

- Ultrasound Amplifier
  - Transducer Types
    * Fluid dynamics: blood velocity
    * Intravascular
  - Generate sound waves and measure reflection
  - Blood Flow
- Audio
- Instrumentation Amplifier
  - Transducer Types
    * Thermocouple
    * Blood Transducer
    * Bridge Amplifier
    * Hall Effect Sensors
  - Arterial Blood Partial Pressure: CO, $CO_2$, $N_2$, $O_2$
  - Peroxide $H_2O_2$ Biosensor
- Differential Amplifier
  - Transducer Types
    * Thermocouple, Thermistor
  - CJC compensation
- Isolation Amplifier
  - Transducer Types
    * Thermocouple
  - CJC compensation

Fig. 8

Sensor Preamplifier Interface Modules

| High Impedance Amplifier | Array of Electrodes | Potentiostat/ Galvanostat | Audio Amplifier |
| --- | --- | --- | --- |
| Differential Amplifier | Bridge Amplifier | Optical | Video Amplifier |
| BioAmplifier | Microfluidics MEMS | LAB-on-a-Chip | Attenuation |
| General Purpose Analog | Isolation Amplifier | Ultrasound (see diagram) | User Defined |
| Transimpedance Amplifier | NanoTech Amplifier | NanoTech Amplifier | User Defined |
| Electrical Stimulus Feedback | Instrumentation Amplifier | Measurement Feedback | Protein cell Amplifier |

Fig. 9

System Specifications

Sensor Inputs and Signal Conditioning
Sensor Interface Module      Unlimited different modules Sensor Interface Module Channels:      8 Differential per chip
     16 Single ended per chip Sensor Interface Modules
     High Impedance
     Differential
     Transimpedance
     BioAmp
     Bridge
     Ultrasound
     Instrumentation
     Isolation
     General Purpose ADC-Analog and Digital      12 to 24 bits, Precision
     Bipolar, Unipolar options

Power
     Core: 1.8V
     I/O Tolerance: 3.3V

PLL Clock
     40MHz

Communications
USB
RS232/SPI/I2C
Ethernet
SERDES

Remote

---

System Specifications

Outputs
Electrical Stimulator Module

Electrical Stimulator Module Channels:      2 Differential

Electrical Stimulator Vmax      +/-10V
DAC- Digital to Analog Conversion      12-24 bits
MDAC-Multiplying Digital to Analog Conversion      12-16 bits Power Stage V      +/-50V
Power Stage I      +/-300mA

RFID

Fig. 10A

*Other - Input sensors*
- DNA
- Lab on a chip
- Quantum dot bio probes
- Cell/protein amplifier
- Hydrogels
- Biochemical
- Nanobiomaterials
- Nanobioelectronics= Biomaterial + Nanomaterial (or metal)
- Nanomaterial=carbon nanotubes, nanoparticles, nanofibers,
- Biomaterial=enzymes, antigens,DNA
- Biopolymers
- Bacteria
- Electrode Array

*Other - outputs to support*
- Nanomotors
- Nanotransporter
- Stimulus
- Drug delivery

METHOD AND APPARATUS FOR CONFIGURABLE SYSTEMS

CROSS-REFERENCE TO RELATED APPLICATIONS

The invention relates to a flexible analog/digital configuration, preferably on a single silicon or other semi-conductor chip for use in receiving various inputs, processing them, and being able to provide in response an electrical stimuli or control signal which can be generated, for example, by a multi-functional electric stimulator output such as those described in U.S. Pat. Nos. 6,029,090, 6,684,106, and U.S. patent application Ser. No. 11/213,050, all identifying Ewa Herbst as the inventor, the patents and patent application being incorporated herein by reference, in their entireties.

This application is a continuation of International Application No. PCT/US2009/066463, filed Dec. 2, 2009, which claims the benefit of and priority under 35 U.S.C. §119(e) to U.S. Provisional Patent Application No. 61/119,244, filed Dec. 2, 2008, which are hereby incorporated by reference herein in their entireties. This application is also a continuation-in-part of U.S. patent application Ser. No. 13/085,366, filed Apr. 12, 2011, now U.S. Pat. No. 8,365,122 which is a continuation of U.S. patent application Ser. No. 12/113,200, filed Apr. 30, 2008, now U.S. Pat. No. 7,937,683, which claims the benefit of U.S. Provisional Patent Application No. 60/926,954, filed Apr. 30, 2007, which are hereby incorporated by reference herein in their entireties. This application is also a continuation-in-part of U.S. patent application Ser. No. 12/485,855, filed Jun. 16, 2009, now abandoned which claims the benefit of U.S. Provisional Patent Application No. 61/129,285, filed Jun. 16, 2008, which are hereby incorporated by reference herein in their entireties.

GOVERNMENT RIGHTS

This invention was made with government support under grant R44 RR021814 awarded by the National Institutes of Health. The government may have certain rights in the invention.

COPYRIGHT NOTICE

A portion of the disclosure in this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

1. Field of the Invention

The invention relates generally to a flexible analog/digital configuration, the system being preferably on a chip, and used for receiving various inputs, processing them, and being able to display/communicate the results and/or provide a response thereto. The invention also relates to a user-configurable instrument designed as a system on a chip (SoC) or as a stand-alone, handheld, user-wearable, or implantable device with functionality defined through a Graphical User Interface (GUI) or other methodology.

The invention also relates to analysis methods and equipment, and in particular to measurement, diagnostic, and treatment equipment able to perform any or all of the functions substantially simultaneously or in a prescribed order. It allows not only for immediate testing but also for long term monitoring of a disease, and for treatment in response to such monitoring, as well as for monitoring of treatment efficacy, which can have importance both for personalized medicine and for drug discovery.

2. Status of Prior Art

The medical device field for measurement, analysis, and treatment of the human (and non-human) condition has grown substantially over the past years as the ability to build customized equipment, easily and quickly using specialized chips, has enabled both large and small companies to enter the field. Of particular interest has been the use of so-called "biomarkers", each of which can be defined to represent a specific measurement or series of measurements, representative of a specific condition or function of the biological system. Other measurements of parameters such as blood gases (e.g., $pO_2$, $pCO_2$), pH, electrolytes, temperature, measured bodily electrical signals (e.g., EKG, EEG, EMG), etc are often made independently of biomarker measurements.

Biomarkers may be associated with a particular disease, or with a range of diseases, or alternatively with a series of predefined biomarkers as dictated by the user. Methods such as genomics, proteomics, and/or molecular imaging, among other methods, can be used in the generation of the biomarker information. Among specific methods used, a variety of spectroscopic methods can be applied, such as fluorescent spectroscopy and mass spectroscopy, which can be used, e.g., for gene expression profiling, Raman spectroscopy and lately Fourier transform infrared spectroscopy (FTIR).

Substantial quantities of data relating to biomarkers and other parameters regarding the human condition such as blood gases, pH, electrolytes, temperature, electrical signals and the like, have been collected for many specific diseases of the body. Also automatic test equipment has been marketed and has been, typically, measurement driven. Equipment is available for measuring pH, oxygen, and temperature at various parts of the body, and various biological measurement schema which are intended to measure, for example, sugar levels, blood counts, the presence of various genes, proteins, acids, etc., and so on are also available. Such equipment is available from many different vendors and provides in many cases, excellent results for the measurement for which they were designed. It is then, typically, up to the doctor or an automated analysis device, which is used by the lab or the doctor and into which selected data is provided, as requested by the doctor, to provide a diagnosis of the patient.

Similar advances are being made in connection with non-human measurement and analysis, as well as in the measurement and analysis of environmental "parameters" (for example, quality of water) in an effort to improve and automate the analysis and resulting diagnosis and conclusions relating to the input data.

Semiconductor manufacturing technology has progressed substantially to allow more custom definitions of systems on a single chip. Nevertheless, researchers in many fields, including, without limitation, biological and medical sciences, and physiotherapy, and clinicians who make use of electrical stimulators and sensors for activities in which they engage, seek further instrumentation which enables them to treat patients with specialized and customizable equipment, but at a reasonable cost, in conformance, for example, with established industry guidelines. Such equipment, while often available at high price and for specialized purposes, often does not meet the needs of these workers. As a result, those working in these and other fields of endeavor are limited in their ability to quickly react to and provide for either patient use or experimental use systems meeting their needs. Further, by "patient", we mean, as used in its broadest sense, human and non-human mammals and other animals, as well as plants (i.e. multicellular organisms), tissues and cells (aggregate and single cells).

Accordingly, it is desirable to find a method and apparatus to enable such workers to quickly generate and use systems meeting their electrical stimulation and input receiving needs without undue delay or cost. In addition, such systems need to be able to be produced as both one of a kind systems, as well as in production quantities in order to satisfy current needs.

SUMMARY OF INVENTION

In one aspect, the invention relates to a method and device to define and control the design of a configurable chip module, for example, for measurement, control and communication systems (for example, for biomedical applications), or any part thereof. The module may include one or a plurality of chip elements. This can be achieved using, for example, a Graphical User Interface (GUI), by transforming selections made by the user to a hardware and/or software configuration for the system. This enables implementation of a plurality of devices and larger subsystems, for example, measuring devices and subsystems, directly on a chip or a chip module without specific semiconductor design know-how from the user. This transformation process is accomplished transparent to the user, who operates the GUI only, and defines the measurement or action which needs to be performed (such as patient treatments); and which, in turn, results in an automatic combination of hardware and/or software elements available to create a specific configuration.

In another aspect, a configurable semiconductor chip module system has analog elements, digital elements, and connection elements between the analog and digital elements. Ones of the analog and digital elements receive inputs from respective sources, and ones of the analog and digital elements output signals for generating control signals having selected electrical and time spatial properties. The connection elements are configurable after creation of the analog elements, the digital elements, and the connection elements.

In another aspect, a configurable semiconductor single chip module for use in patient treatment has analog elements, digital elements, and connection elements between the analog and digital elements. Ones of the digital and analog elements receive analog inputs from respective sources, and ones of the digital and analog elements output signals for controlling control signals having selected electrical and time spatial properties useful in medical treatment. The connection elements are configurable after creation of the analog elements, the digital elements, and the connection elements.

In a further aspect, a passive (that is, without feedback) configurable semiconductor single chip module for use in making analytical measurements of parameters related to patients' status has analog elements, digital elements, and connection elements between the analog and digital elements. Ones of the analog and digital elements receive analog inputs from respective analog sensors, and ones of the analog and digital elements output signals relating to measurements from the sensors. The connection elements are configurable after creation of the analog elements, the digital elements, and the connection elements.

A method of the invention for manufacturing a flexibly configurable semiconductor single or multiple chip module for receiving and outputting various signals not specifically known at the time of manufacture: manufactures a plurality of analog elements, digital elements, and connection elements between said analog and digital elements; enables ones of the analog and digital elements for receiving inputs from respective sources, ones of the analog and digital elements for outputting signals for generating or controlling control signals having selected electrical and time spatial properties; and configures the connection elements after creation of the analog elements, the digital elements, and connection elements, to configure the module.

In yet another aspect, the invention relates to a method and device to define and control functionality of measurement, control and communication systems (for example, for biomedical applications), or any part thereof, using for example a Graphical User Interface (GUI), by transforming selections made by the user to a hardware and/or a software configuration for the system. This enables implementation of a plurality of devices and larger subsystems, for example, measuring devices and subsystems, without requiring an engineering expertise from the user. This transformation process is accomplished transparent to the user, who operates the GUI only, and defines the measurement or action which needs to be performed (such as patient treatments); and which, in turn, results in an automatic combination of hardware and/or software elements available to create a specific configuration. This therefore enables the user to perform without "technical know-how," a specific measurement, a series of measurements, a treatment or another operation.

BRIEF DESCRIPTION OF DRAWINGS

Various objects, features and advantages of the present invention can be more fully appreciated with reference to the following detailed description of the invention when considered in connection with the following drawings, in which like reference numbers identify like elements:

FIGS. 7 and 8 are charts illustrating various flexibilities available in constructing elements described herein in accordance with an embodiment of the invention.

FIG. 9 illustrates various sensor-interface modules in accordance with embodiments of the invention.

FIGS. 10A and 10B illustrate a typical system specification for various elements of a system for enabling operation of a module and its manufacturing construction, in accordance with the embodiments of the invention.

FIGS. 11-34 illustrate screen shots of operation of a graphical user interface in accordance with embodiments of the invention.

DETAILED DESCRIPTION

Figure 1:
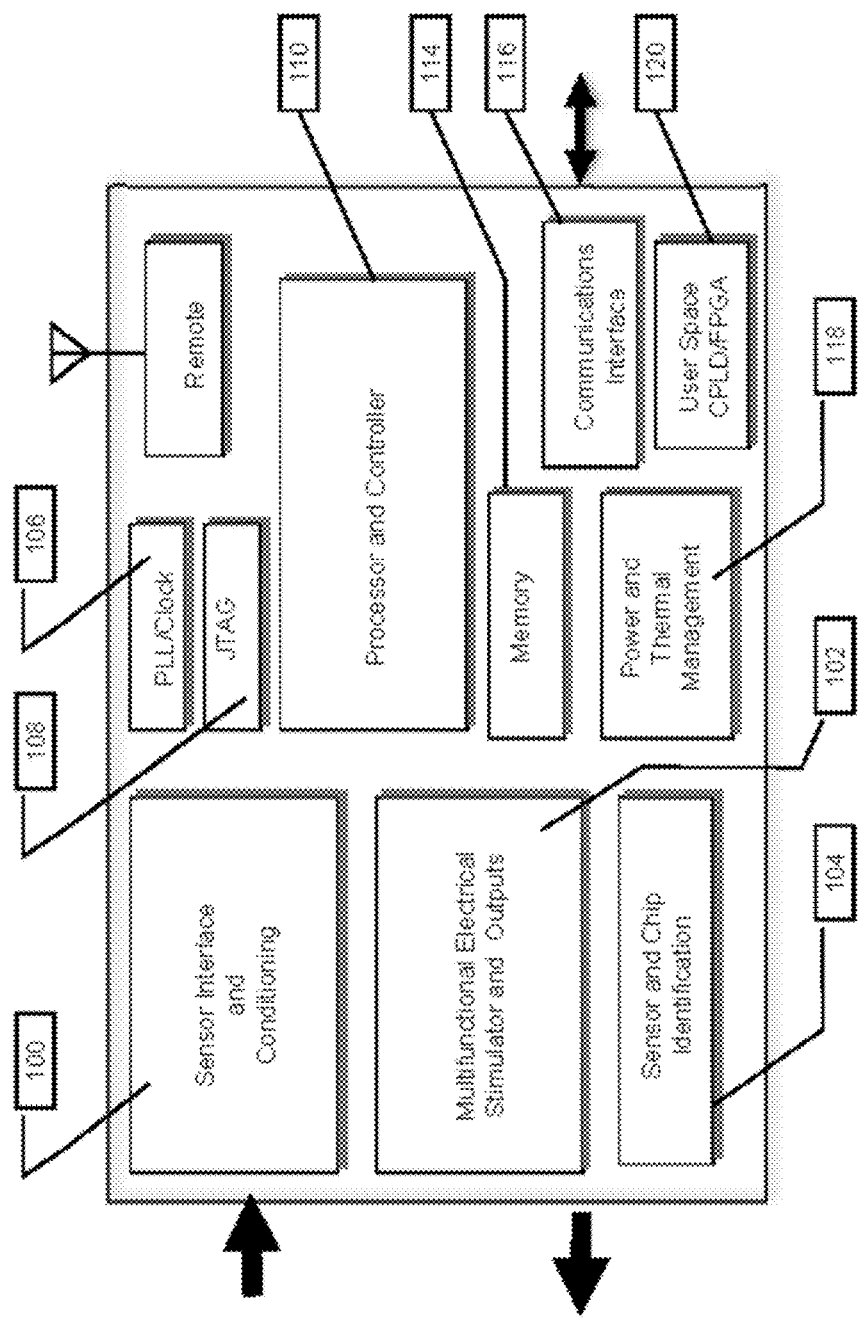
FIG. 1 describes a general block functionality in accordance with embodiments of the present invention.

The general block functionality of an embodiment of the invention is illustrated in FIG. 1. Referring to FIG. 1, the system includes a sensor interface and conditioning module 100, a multi-functional electrical stimulator and output module 102, a sensor and chip identification module 104, a phase-lock loop clocking module 106, a JTAG module 108, a processor and controller module 110, a memory module 114, a communications interface module 116, a power and thermal management module 118, and a user-programmable module 120, which can be implemented as CPLD/FPGA. These elements are designed in particular to be incorporated on a single chip such as a configurable application specific standard product (ASSP) which has for example a plurality of fixed layers, on top of which several layers can be placed to customize the chip and to allow interconnections as desired between elements or modules in the fixed layers. Thus, for example, elements 100-118 might be the fixed elements on the chip and the user space would be several layers on top of the fixed layers to effect connections, additional elements needed for the chip, etc. Other chip or multichip configurations could be used as semiconductor manufacturing methods are developed or to minimize the manufacturing cost, for example, separating analog and digital functions between two chips. Further, the layers can be fixed with programmability features as known in the field.

A "system on a chip" (SoC) advantageously can measure multiple parameters; and when properly programmed, can easily organize the data from multiple sensors or other analog or digital sources. It can present or display different, or similar, pages for setting up each measurement (or each measured parameter), for example by sensor, class of sensors, etc., to enable an easy to use approach for non-technical individuals without needing to know the specifics as to many parameters. This user-friendly and lower-cost approach further enables the measurement and interconnection to be performed using a configurable standard basic chip according to the invention. FIGS. 11-34 and the related description describe one illustrative approach, using an easy to use GUI for configuring the system for desired measurements and analyses.

Figure 2:
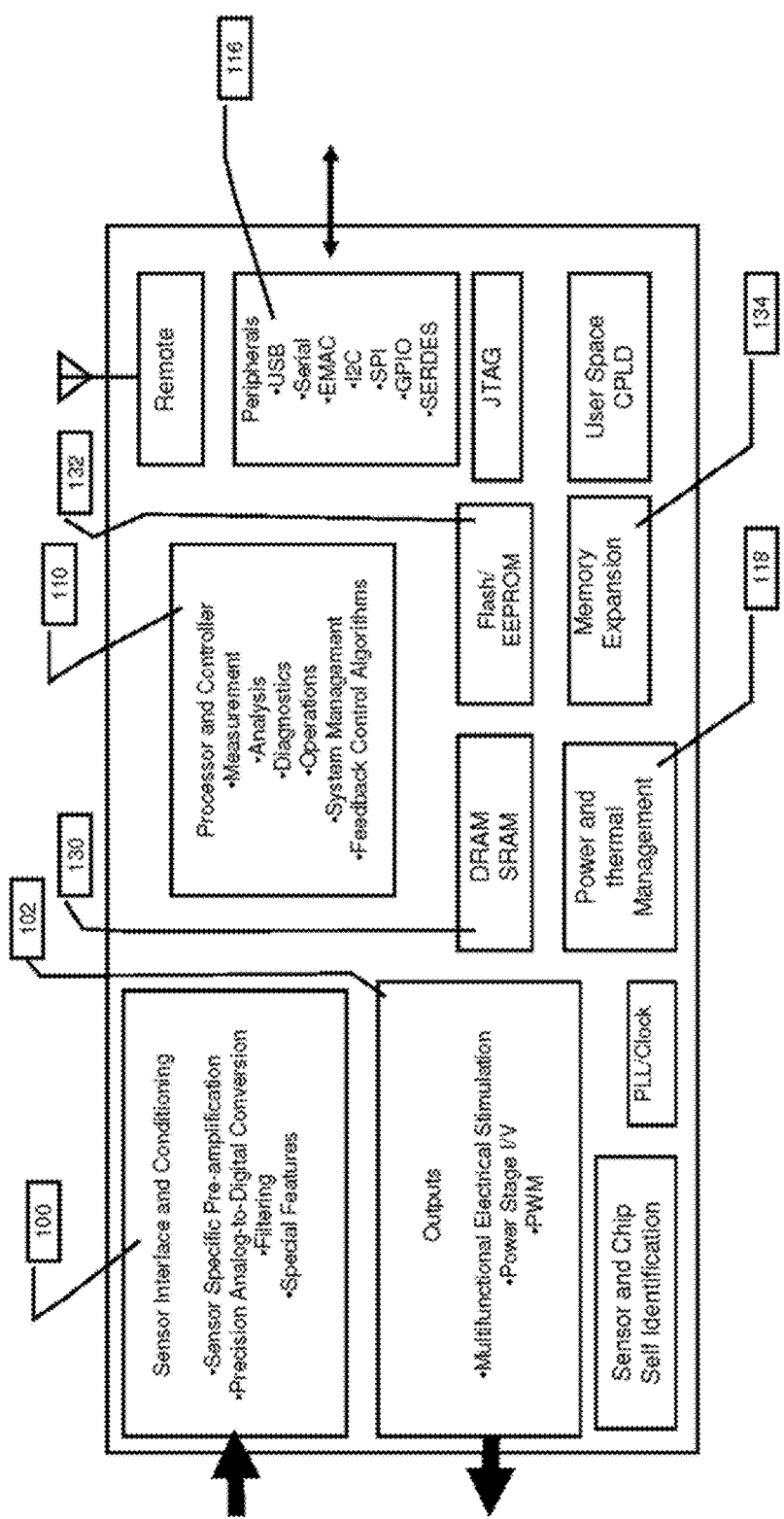
FIG. 2 illustrates a more detailed view of the general block functionality in accordance with one embodiment of the invention.

Considering the modules of FIG. 1 in more detail, and referring now to FIG. 2, the sensor interface and conditioning module 100 can include sensor-specific preamplifiers, precision analog-to-digital conversion circuitry, filters for filtering the signal inputs, and other special features depending upon the particular application to which the circuit is put. And, as described in more detail below, various components can be connected to be grouped as a family, for example by sensor functionality or characteristic, such as impedance, signal levels, etc., to more efficiently connect the analog and digital elements of the modules, in a chip layer, or between chip layers. This can also result in a smaller chip/module footprint.

The processor and controller module 110 is thus programmable by the user and/or configurable in hardware, using, for example, the GUI of FIGS. 11-34, to perform the functions of measurement, analysis, diagnostics, operations, and system management, and to enable feedback control algorithms as required. Each of these functions can be the subject of software applications which are stored in memory 114 (FIG. 1). Memory 114, in some embodiments, includes a DRAM and/or SRAM module 130, a flash or EE PROM memory 132 and can have available space for memory expansion 134 (FIG. 2). The multi-functional electrical stimulator and output module 102, in addition to providing a multi-functional electrical stimulation unit, such as that described in the Herbst patents and patent application identified above, can also provide a power stage for controlling current and voltage as well as a pulse width modulator stage (PWM) for effecting the outputs of the module 102. Furthermore, the communications interface 116 can communicate to various peripherals using video, audio, or any of a number of protocols, all of which can be supported by a suitable design on the chip. Those protocols can include, for example, USB, Ethernet, I2C, SPI, GPIO, user communications protocols, SERDES protocols. Other protocols, as they are developed or as they are required by the user, could also be either preprogrammed into the hardware or programmed into the software depending upon the particular design of the chip or chip set. Further the "peripherals" can include servers and server interfaces, and functions of the electrostimulator module, for example, power, sensing/sensors, feedback controls, and protocol conversions.

Figure 3:
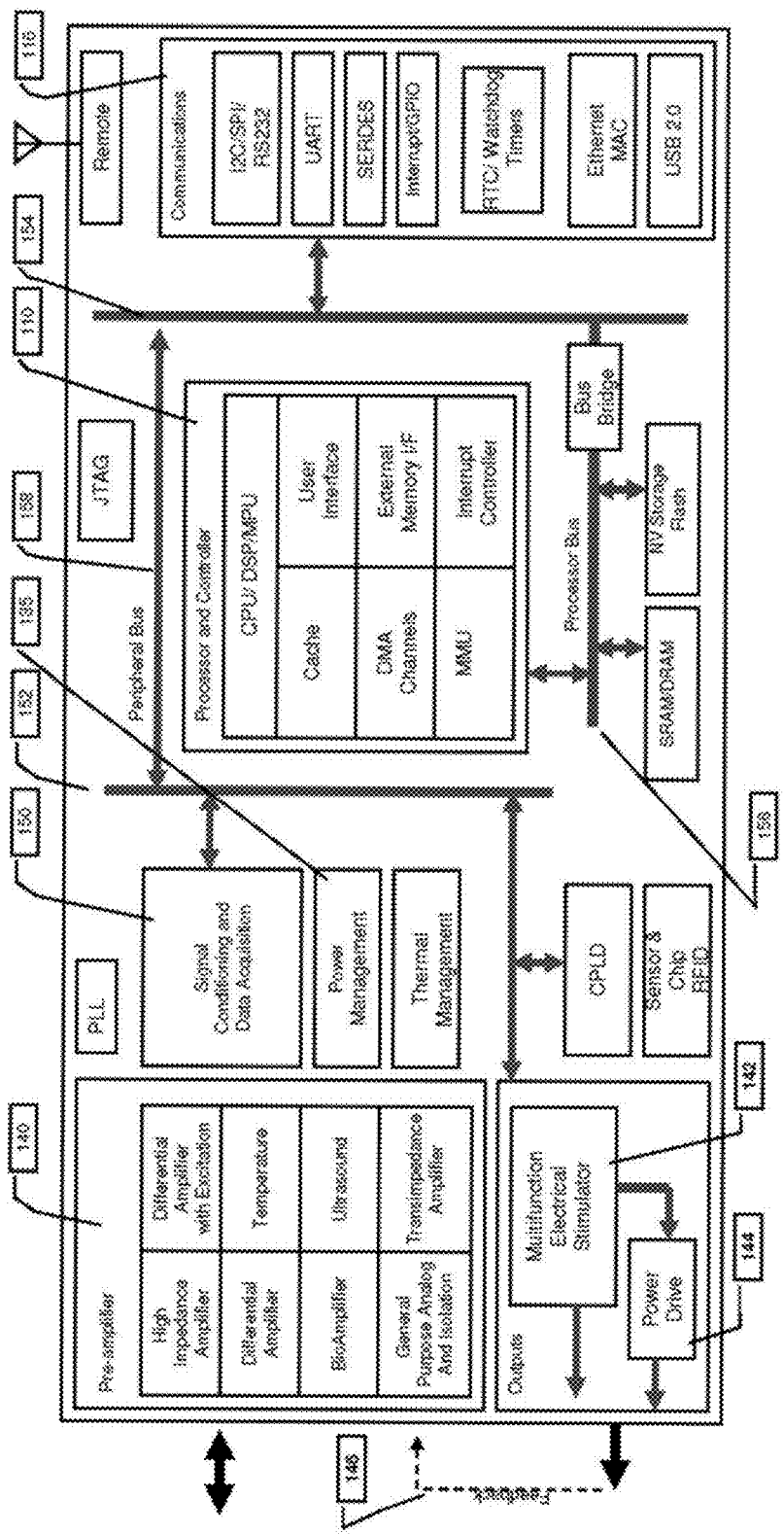
FIG. 3 illustrates in more block level detail, an embodiment of elements of the system on a chip and details as to the acronyms relating to various of the elements.

Referring now to FIG. 3, which illustrates in more block level detail one embodiment of the elements of a system on a chip and which provides detail as to the acronyms related to various of the elements, the sensor interface and conditioning module preamplifier section 140 can include any (or all) of a number of amplifier types such as a high impedance amplifier, a differential amplifier with or without excitation, a temperature amplifier, a bioamplifier, an ultrasound amplifier, a transimpedance amplifier, and generally a general purpose analog amplifier with or without isolation.

The multi-functional electrical stimulation and output module 102 can have in particular an output section which enables the multi-functional electrical stimulator 142 in a manner comparable to that described in the patents identified above to generate output signals in response to instructions or control signals from the processor and/or controller, the signal conditioning and data acquisition module, or the user-programmable module. The output of the multi-functional electrical stimulator can be provided directly to output receiving elements (not shown) or through an amplifier or power drive 144 to such receiving elements. In a particular embodiment, outputs from the output module can be fed back (146) as an input to the sensor interface and conditioning module 100 through a separate process to help provide closed-loop control of the output stimulation signals. The output module 102 can also be used to generate desired output signals in response to, for example, user programming.

In a specific example, a system can be created as a general voltage/current measurement system, a biosensor based system, an environmental measurement system, or a gas measurement system; and any of the above systems with a feedback control mechanism, to influence an outcome such as a specific treatment scheme or regiment, for example electrical stimulation or drug delivery, and where as any of the above have communications elements and especially wireless communication elements.

The signal conditioning in data acquisition portions 150 of the sensor interface and conditioning module 100 connect to a first bus 152 which in some embodiments connects also to a peripheral bus 154.

The processor and controller module 110, referring to FIG. 3, is further broken down to show various elements of the module 110. The module may include many of the "standard" elements of a standard processor including the CPU or digital signal processing element or multiple processing unit, cache, a user interface module, a direct memory access (DMA) channel or channels, a memory management unit (MMU), an interrupt controller, and an external memory interface. These can be connected through a processor bus 156 to various portions of the memory, such as SRAM, DRAM or the non volatile (NV) storage flash memory. In the illustrated embodiment, the processor and controller module 110 has two processor bus elements 156 and 158 which connect to bus 154. The communications interface module 116 connects to bus 154. As illustrated, the communications module can have, in addition to the elements identified in connection with FIG. 2, a UART, an interrupt/GPIO, an RTC/Watchdog timer, an Ethernet MAC, an optical peripheral device, and the USB protocol identified in FIG. 3 as USB 2.0. FIG. 3 also sets forth many of the acronyms used in the figure for convenience.

Figure 4:
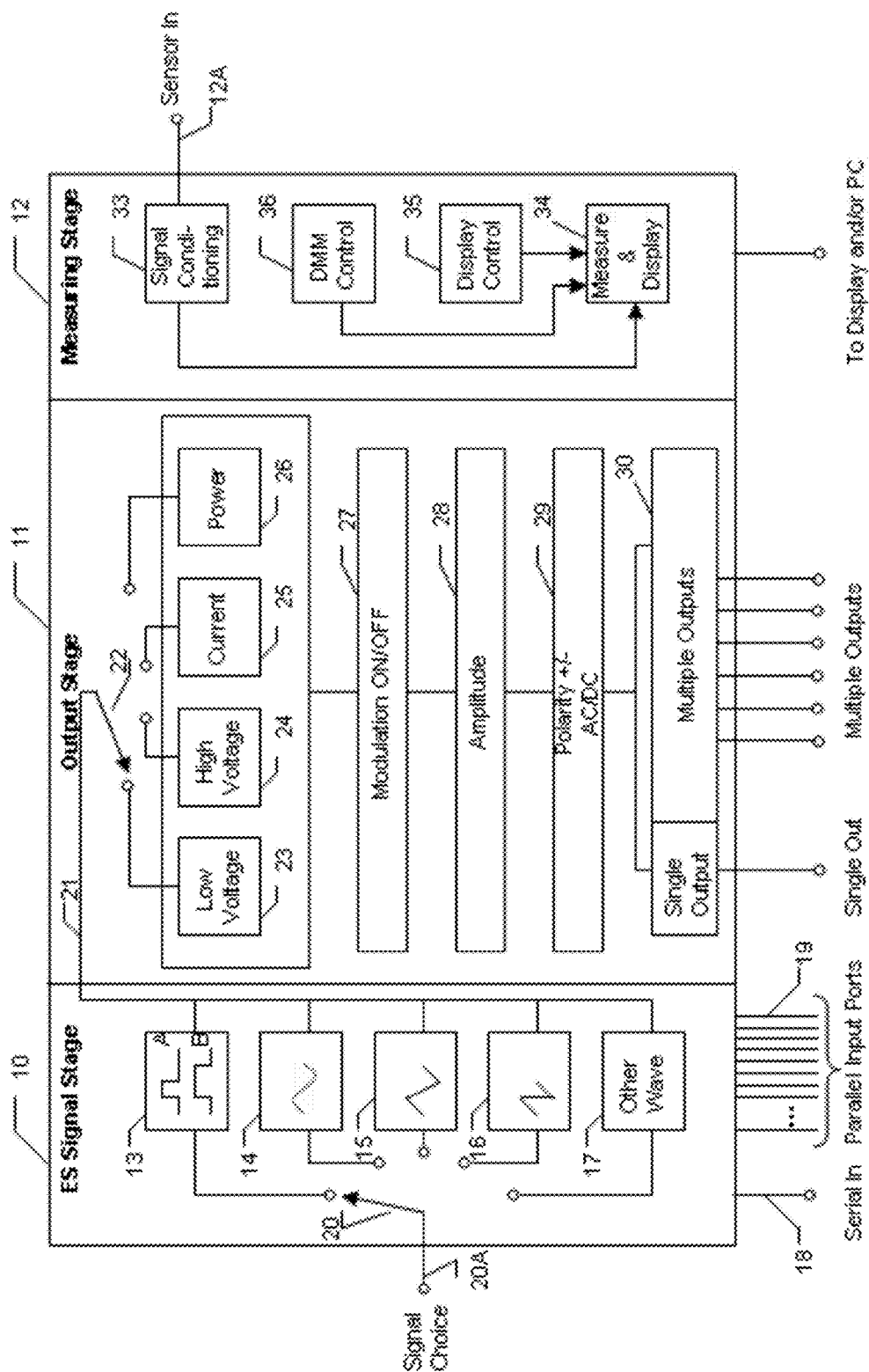
FIG. 4 illustrates a multifunctional stimulator in greater detail.

Referring now to FIG. 4, the multi-functional stimulator is shown in greater detail with reference to the multi-functional stimulator described in the above-identified patents. The reader is referred to, for example, U.S. Pat. No. 6,029,090 for a more complete and detailed description and understanding of the various elements described in FIG. 4 and which would correspond substantially to portions of module 102, referring to FIG. 1.

Figure 5:
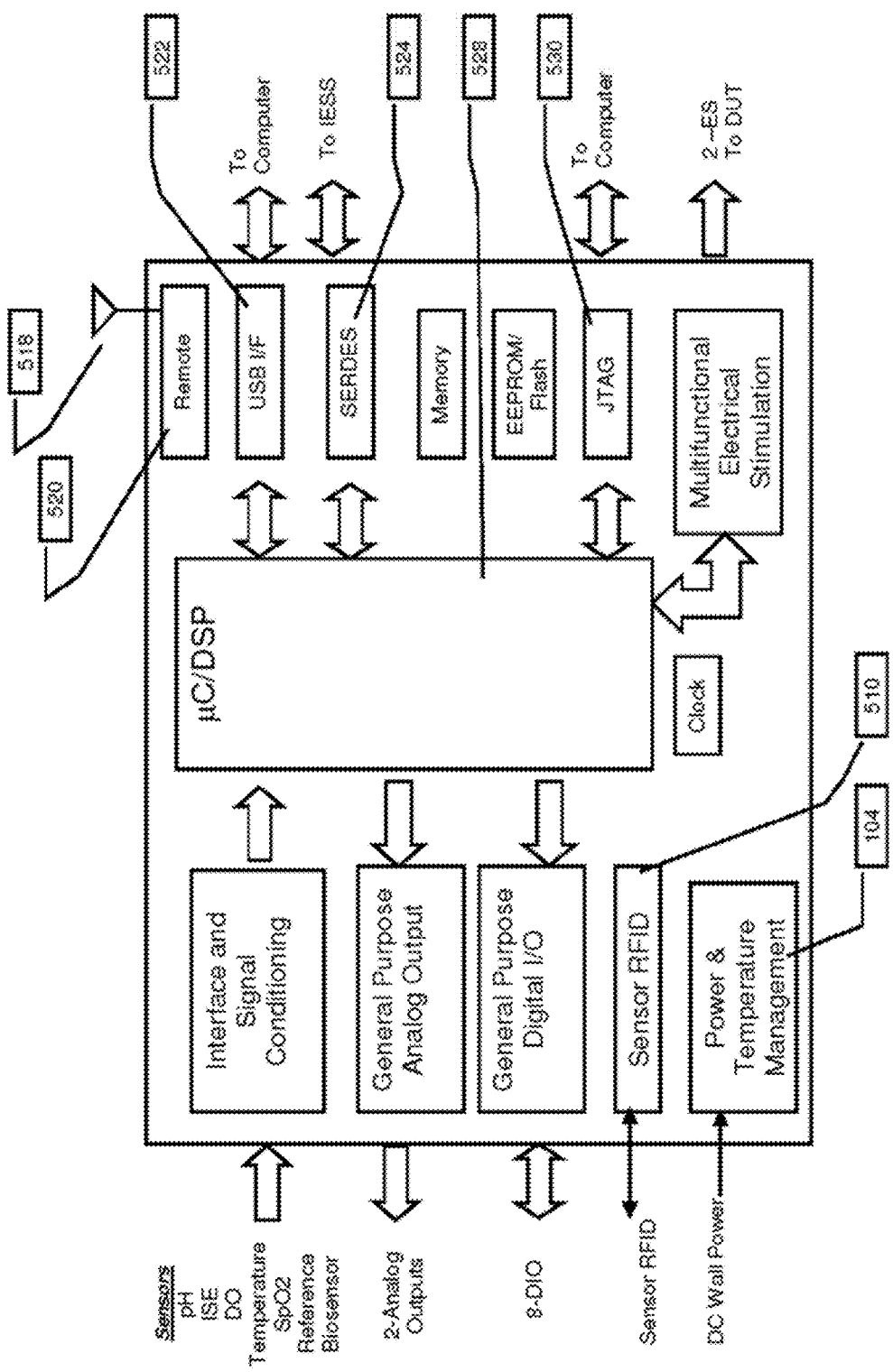
FIG. 5 illustrates a particular implementation of the system on the chip in accordance with an embodiment of the invention.

Referring now to FIG. 5, there is illustrated a particular embodiment of the system showing the general interconnection and operation of the various components, and including some specificity with regard to the sensors which might be connected to the interface and signal conditioning, the ability to provide two analog outputs and eight digital outputs, as an example, the use of a sensor RFID module 510, and using the power and temperature management module 104 across the chip. On the other side of the chip or module, the ability to wirelessly connect to the module through antenna 518 and remote sending and receiving module 520 is illustrated. Alternatively, a computer can be connected to the module through USB IF (USB interface) element 522. Other interface connecting signals in this illustrated embodiment are provided through the serial deserializer 524. The multi-functional electrical stimulator is illustrated as being controlled by the microcontroller or DSP 528 and provides outputs as illustrated. The JTAG module 530 for example, connects also to the microcontroller as well as to an external computer.

Figure 6:
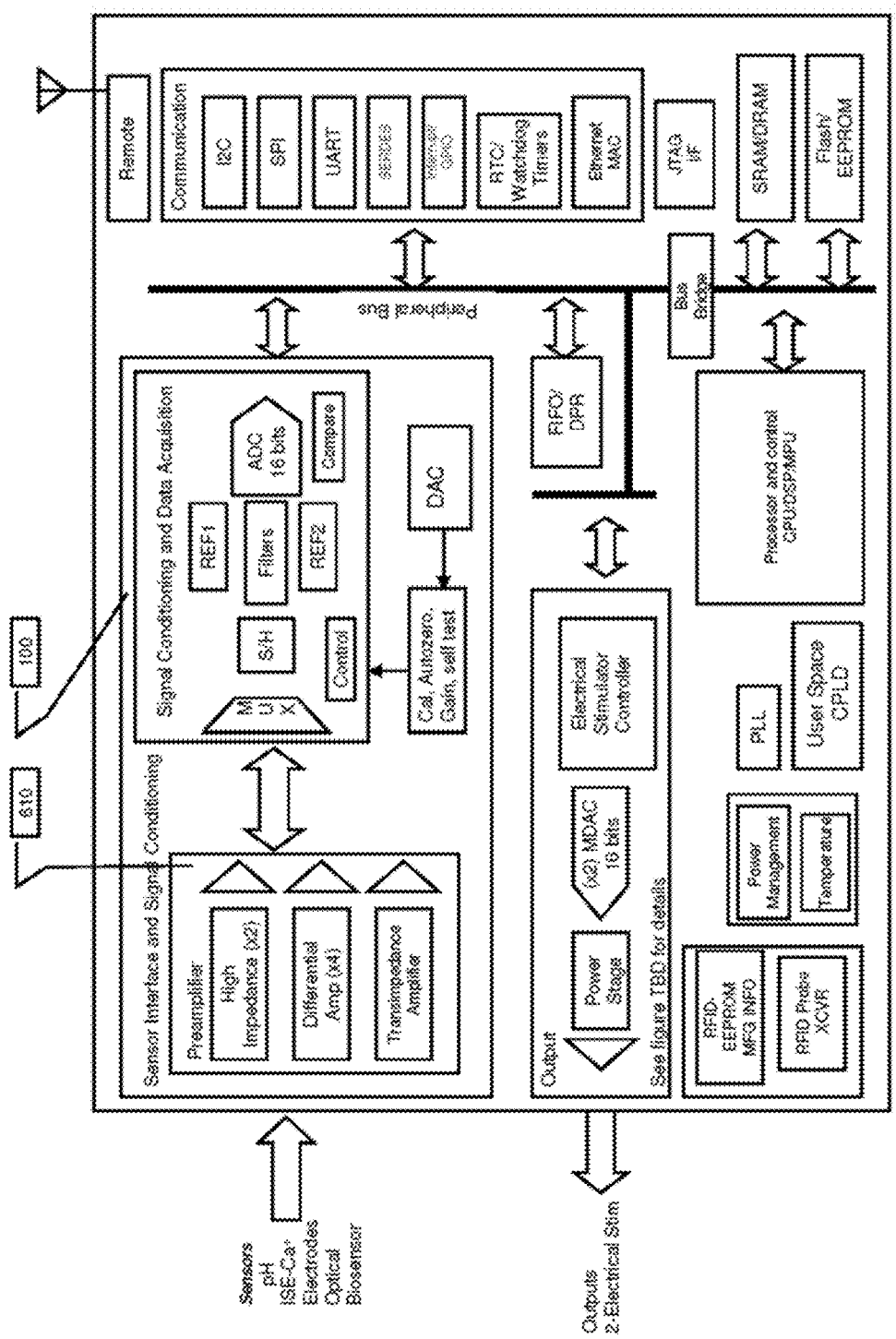
FIG. 6 illustrates details regarding an exemplary sensor interface and conditioning module.

Referring now to FIG. 6, further detail is provided with regard to an exemplary sensor interface and conditioning module 100. As illustrated, different sensors can be provided and treated differently by the high impedance, differential, and transimpedance amplifiers provided in the pre-amplifier module 610. The output of the pre-amplification is sent in some embodiments to the signal conditioning and data acquisition module where it can be multiplexed, sampled, filtered, and converted to a digital value as illustrated, typically, in that module. Various calibration controls are available as illustrated.

The output section contains the electrical controller mentioned above. Various digital to analog converters, here 16 bit DACs, are provided, the output of which is presented to an output stage capable of driving one or more electrical stimulation outputs. Other components illustrated in FIG. 6 are noted and are similar to, if not identical to, the related elements in FIG. 5. The charts in FIGS. 7 and 8, illustrate various flexibilities available in constructing any of the elements hereinbefore. This flexibility provides not only for a very useful and "burnable" circuitry over time, but in addition enables the user to substantially design how the system will work. In that respect, therefore, the elements of FIG. 6, representing the chip-level layer, provide, for these embodiments of the invention, a particularly advantageous methodology for building the chip containing the elements and modules described herein. Thus the modules/functions can be configured by the user (for example who may not need to be technically trained) in response to needed application parameters or as a result of available classes or types of sensors/inputs to create a customized chip; that is, a chip having user-selected chip functions and modules/building blocks. In fact, if this occurs early enough in the manufacturing cycle, a smaller footprint, and perhaps fewer "user" layers may be achieved. This interactive process results in a faster and simpler time to use of the system on a chip (SoC).

In particular embodiments of a typical controller interface, a method for the design of configurable electronic systems, for example, the system on a chip (SoC), for measurement, control and communications (specifically for biomedical applications), or any part thereof, uses a Graphical User Interface (GUI) for transforming input selections made by the user to a hardware and/or software system. These systems include mask-based systems, such as ASSP, as well as one time programmable (OTP), or re-programmable, systems. This allows for implementation of a multitude of devices and larger systems for example measuring systems, directly on a chip, without a requirement for engineering expertise by the user. This is accomplished transparent to the user, who operates the user friendly GUI to define the measurement or action that needs to be performed (such as a patient treatment), which, in turn, results in an automatic combination of hardware and/or software elements available, for example, to create a specific configuration, thereby enabling the user to perform specific measurements, a series of measurements, a treatment or other operation. The hardware elements are chosen automatically in response to the GUI based inputs, from a library of hardware elements, based on required functionality defined by the user. For example, if a user wants to design an instrument which performs pH measurement or measure a specific ion using an ion selective electrode (ISE), and defines the electrode as a glass electrode, the system will automatically choose an impedance buffer on the input to a measurement system due to high output impedance of the glass electrode. This is described in more detail in the GUI description of FIGS. 11 to 34. To reduce power requirements, especially for handheld or implantable devices, only the chosen hardware elements will be connected to a power supply during the configuration process. The hardware elements, for the most part, are functional hardware elements, such as defined in the patent application Ser. No. 12/113,200.

Referring now to FIG. 9, there are illustrated various sensor pre-amplifier interface modules.

Thus, the various sensors and sensor pre-amplifier interface modules are illustrated for various embodiments of the invention. As will be clear to one practiced in this field, various of these modules can be made "standard" for a chip, while others, can be added by the user, depending upon the needs of the user.

Referring now to FIGS. 10A and 10B, there is provided a high level typical system specification for the various elements of the system on a chip and for enabling operation of this flexible module and its manufacturing construction based upon the needs described herein.

Referring to FIGS. 11 to 34, the GUI can be created in any way appropriate to a specific application and implemented on a PC, PDA, embedded web server, or in any other way convenient for the user. An example of such a GUI for a biomedical system technology platform is illustrated in the screen shots of FIG. 11 through FIG. 34. Those figures show screen shots for definition of a measurement and control system for biomedical instrumentation, analytical instrumentation, or biomedical devices or sub-systems based on a user-specific sensor input and desired measuring methodology.

The same, or similar GUI can be used to define hardware (from the library of functional hardware elements) required to perform a desired measurement, or other operation, and to connect the hardware elements using connecting devices described above, to create configurable systems, including an SoC.

In both applications, a user can utilize the GUI to configure number of inputs, outputs, and feedback elements (see FIG. 12), define type and other specifics of inputs (see FIGS. 14-19 and 31-34) and outputs (see FIGS. 20-23), define various settings for feedback (see FIGS. 24-26), etc. Each screen has several drop down menus or sub-screens creating a tree structure, which functions to both define a useful functional methodology for the user (user tree), as well as a hidden operational structure for the instrument, a hardware and/or software configuration for the system, or an automatic SoC design (hidden tree). The hidden tree is not visible to the user and can employ various methods to choose appropriate hardware, software, and connecting elements as described above, to arrive at a user-defined functional solution. For example, for a user-picked voltage level of ±10V. in FIG. 16, the machine generated tree will implement the user selection by choosing an appropriate amplifier to generate an output of ±10V. from a set of available voltage amplifiers. Based on the user choices, there may arise conflicts, such as between amplitude and bandwidth, which in such situations need to be communicated to the user.

Referring now to FIGS. 11-34, there is illustrated a series of screen shots illustrating the process by which a user is enabled to configure the system using the user programmable module through the graphical user interface even though the user may lack the technical know-how not only to understand what is happening within the system, but the details thereof. This particular embodiment shows the graphical user interface for a biosensor measurement system, however the concept of the interface and its actions should not be limited solely to the biosensor measurement environment.

Figure 11:
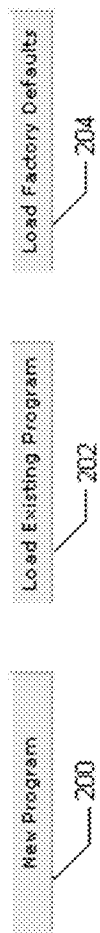
Figure 12:
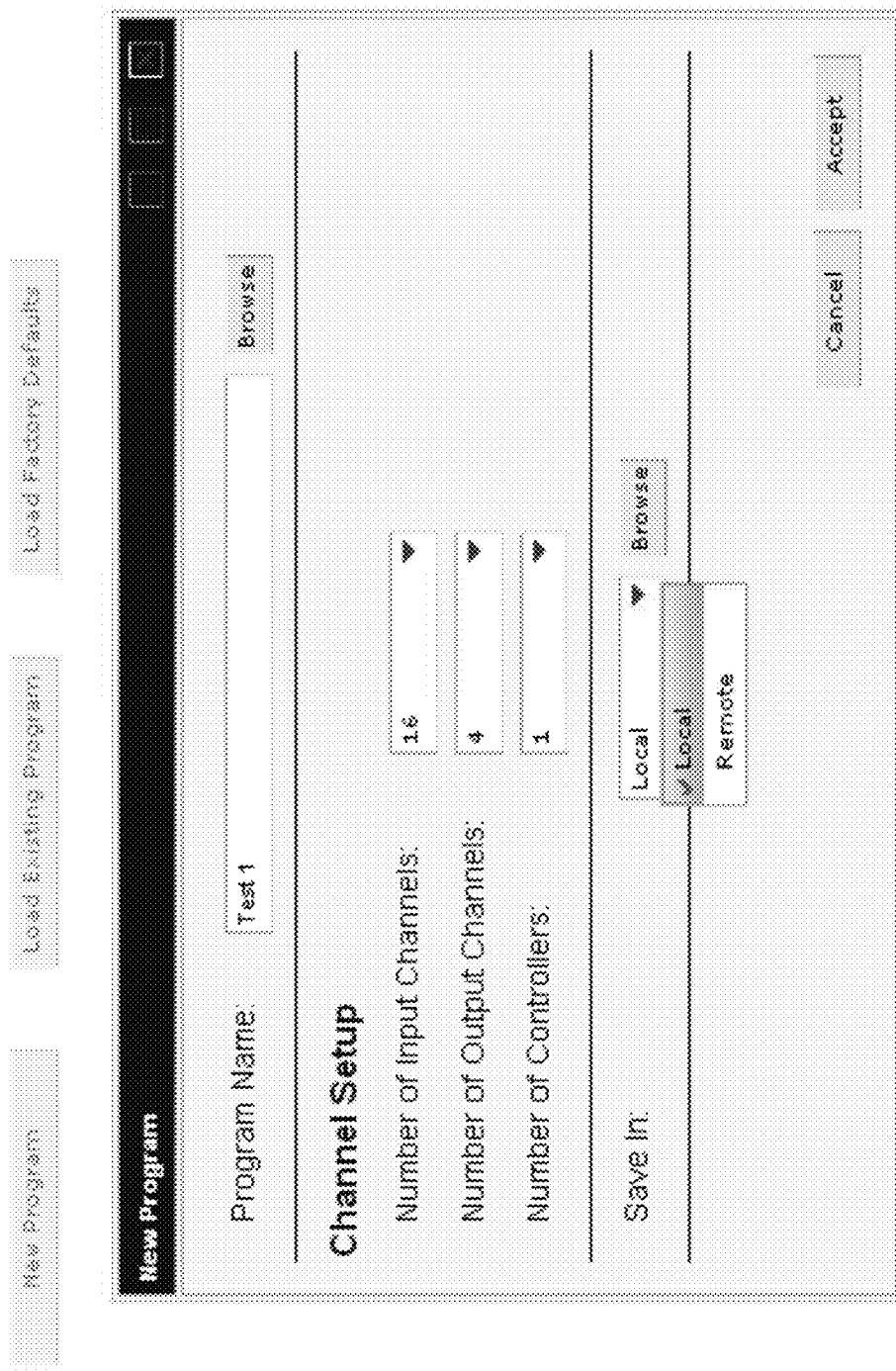
Figure 13:
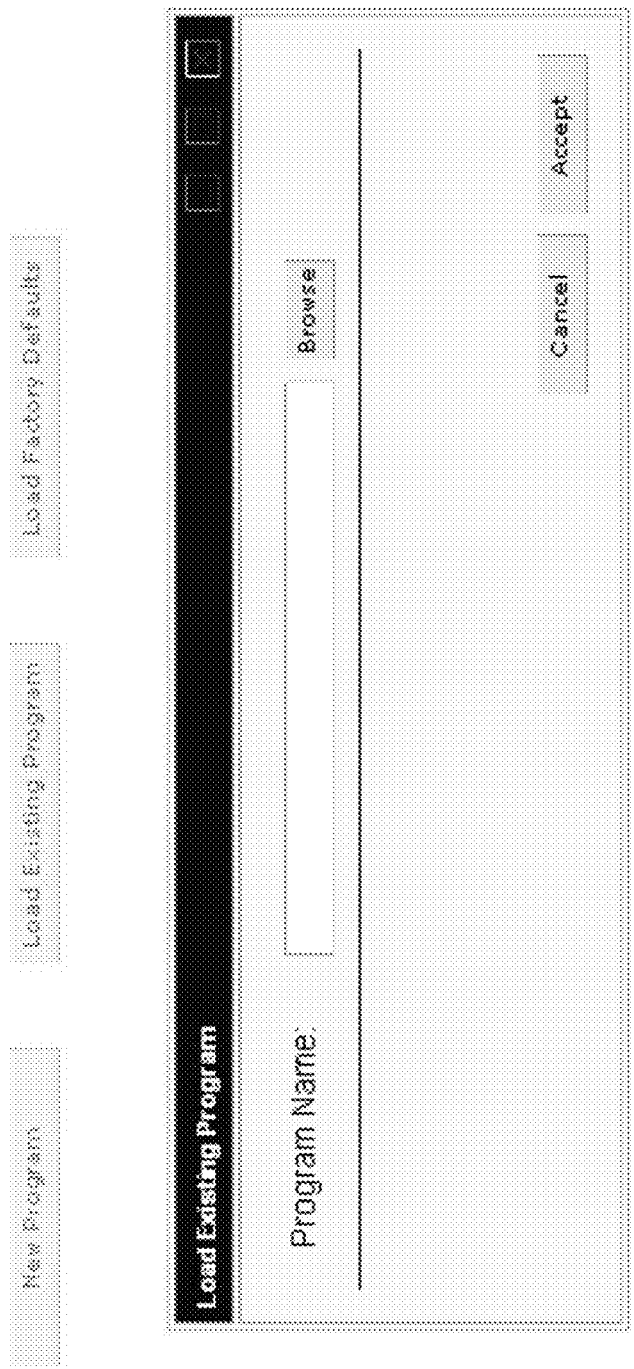
Figure 14:
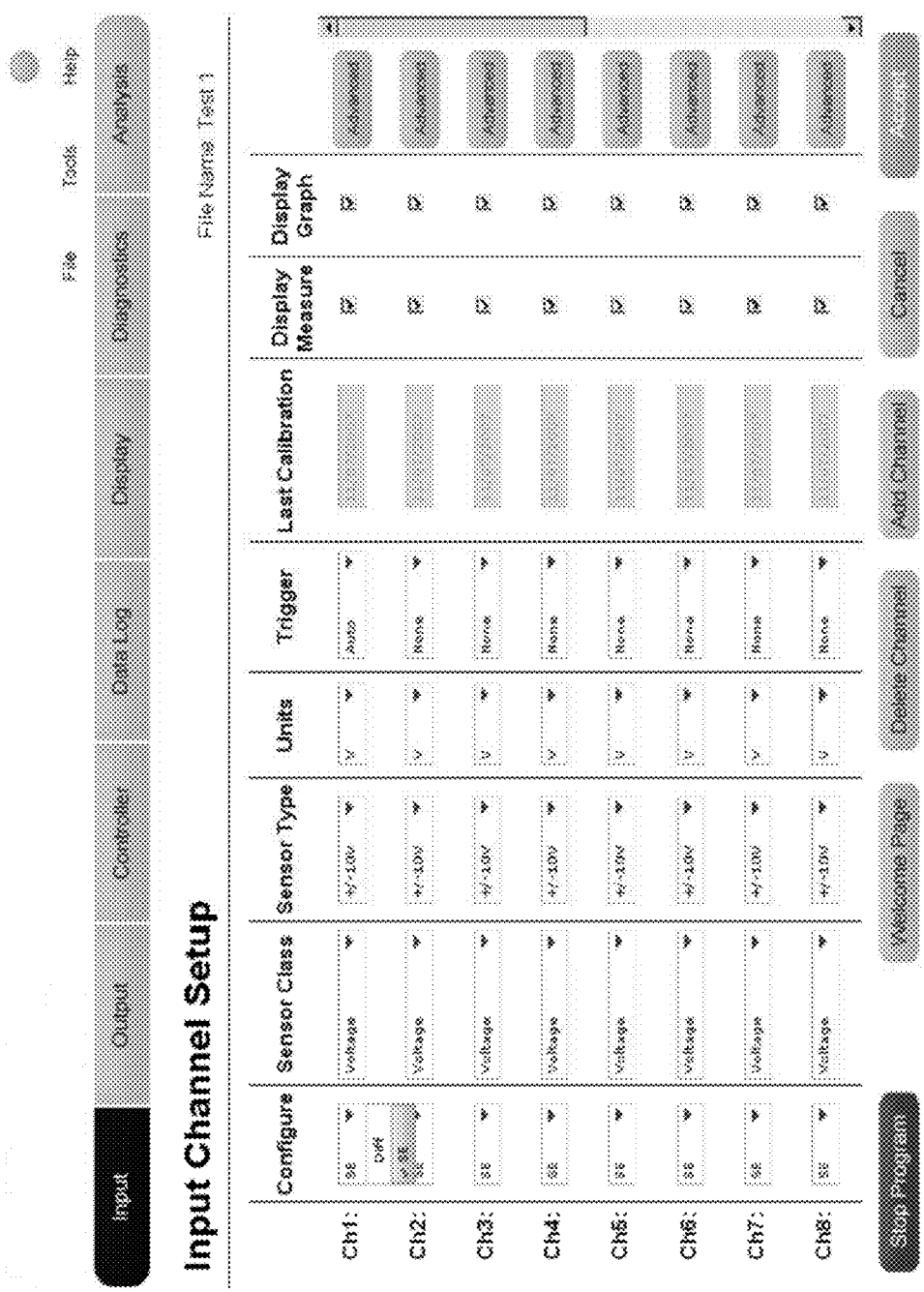
Figure 15:
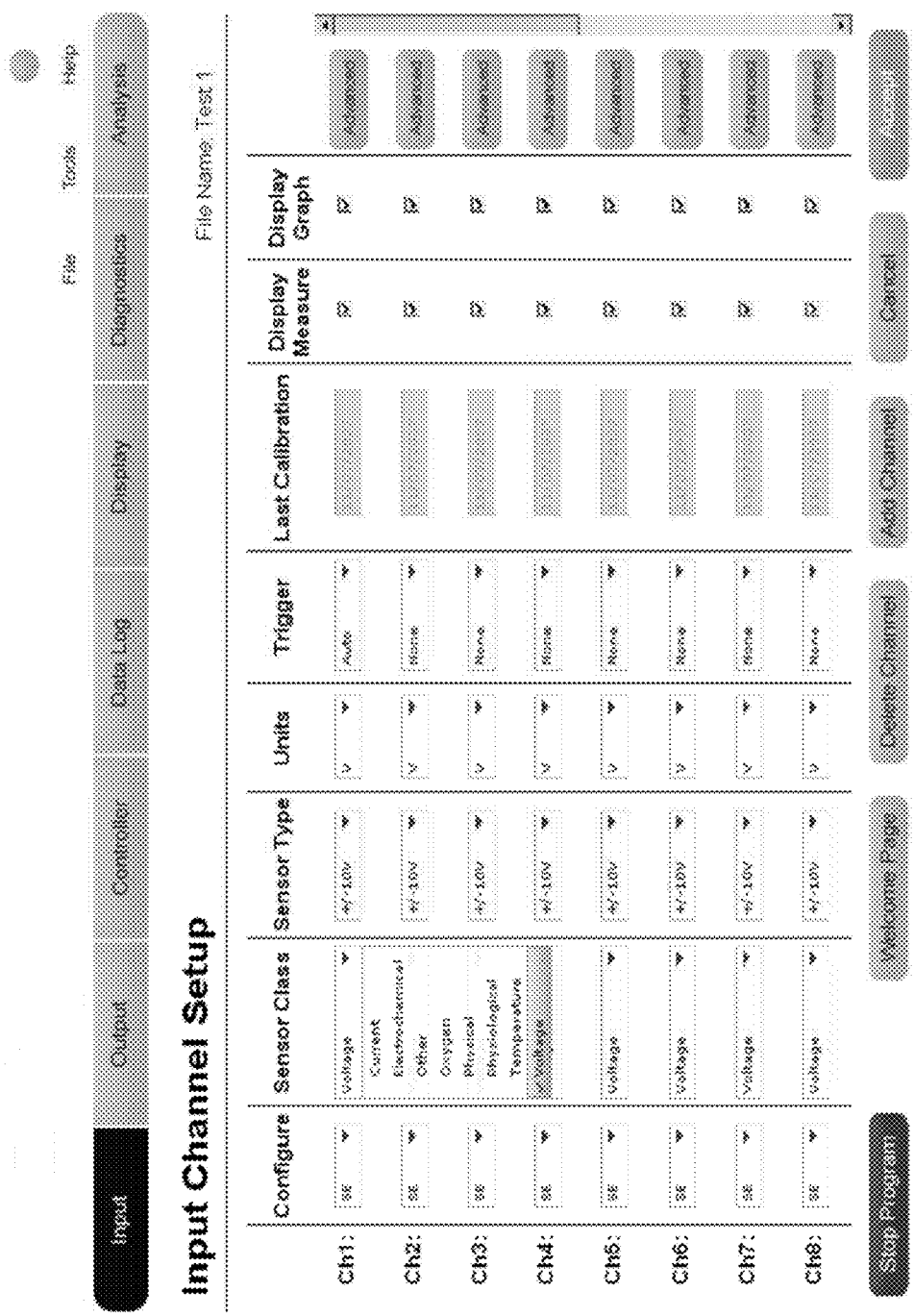
Figure 16:
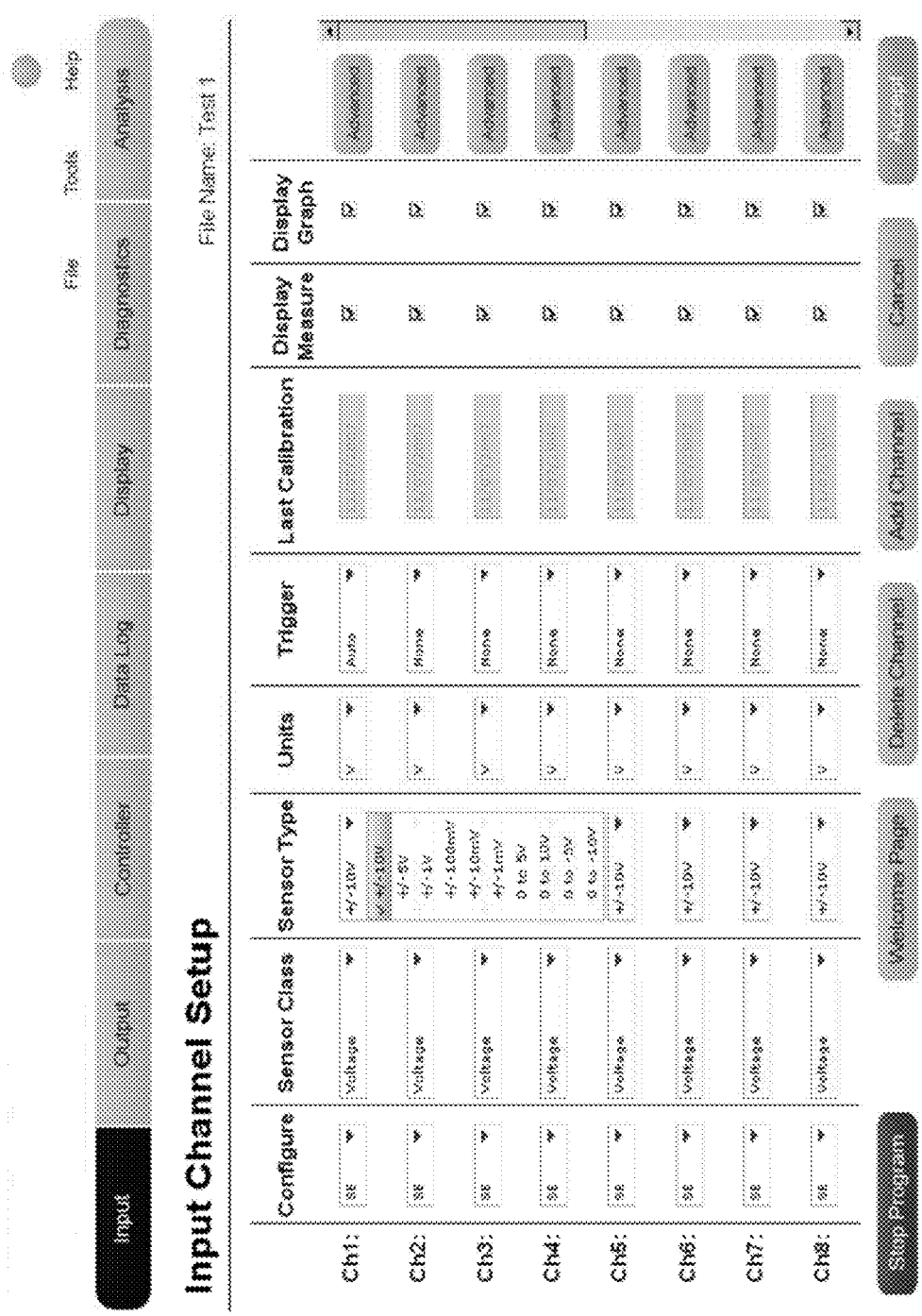
Figure 17:
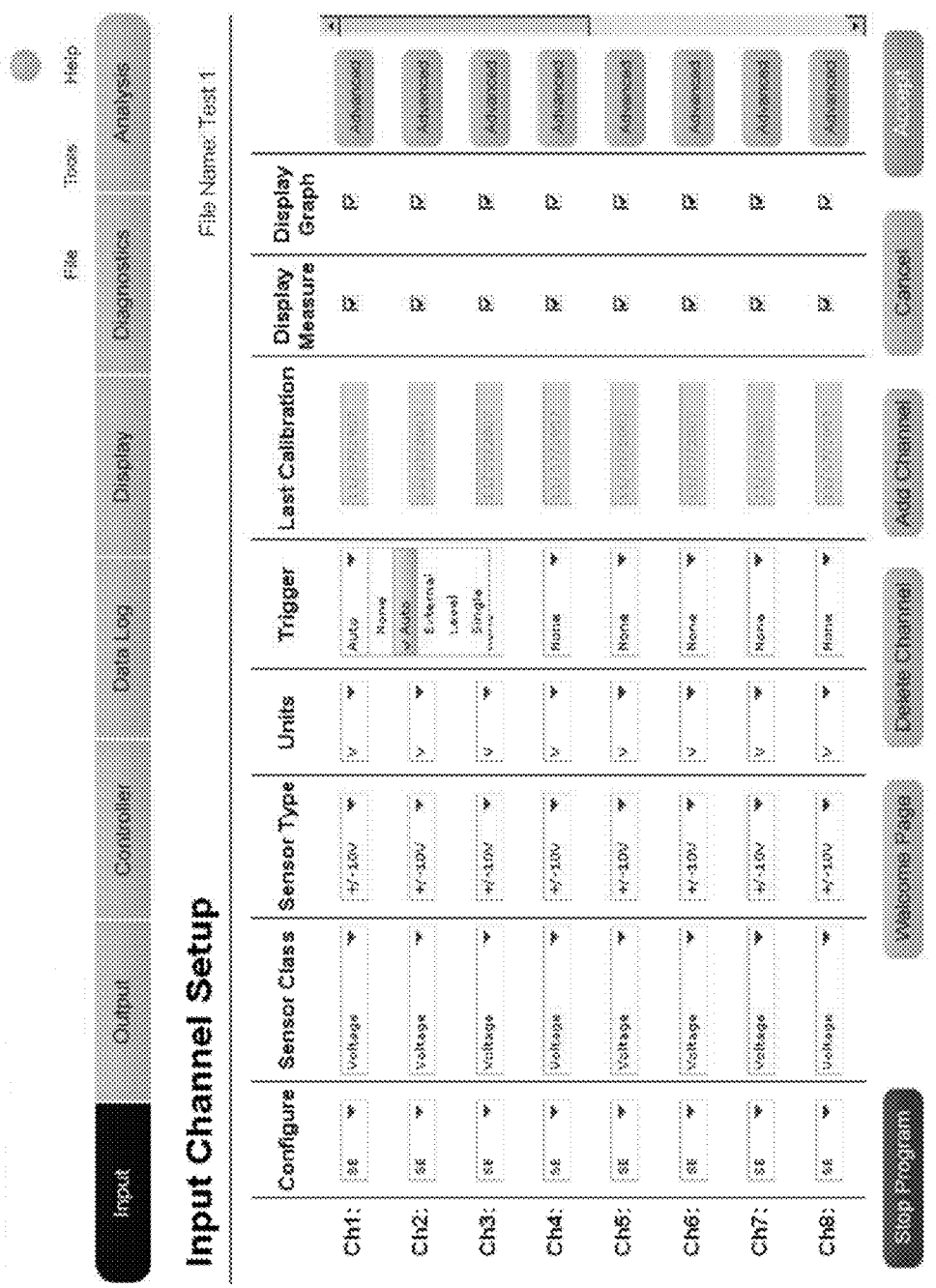

Turning to FIG. 11, there is illustrated a typical sign-on/welcome screen. Once the user signs on, he can load a new program at 200, an existing program at 202, or can use the factory provided defaults at 204. Referring to FIG. 12, if a new program is opened, the user is shown a screen having choices on the number of inputs, outputs, and controllers. The user can save his choices remotely or locally. Referring now to FIG. 13, the user names the program, and in FIG. 14, the user can configure each selected channel as desired. In FIG. 14, the user can configure the channel as single or differential, and in FIG. 15, the user can select the sensor class for each channel. In FIG. 16, the user can select the type of sensor to be used for the channel, and in particular as illustrated, where the sensor class was voltage, the sensor type includes a selectable voltage range. Note that the sensor type is changeable depending upon the sensor class, and whether the channel is single ended or differential. Next, referring to FIG. 17, the trigger option menu is provided for the channel. As illustrated in FIG. 17, the trigger option has been set to "auto".

Figure 31:
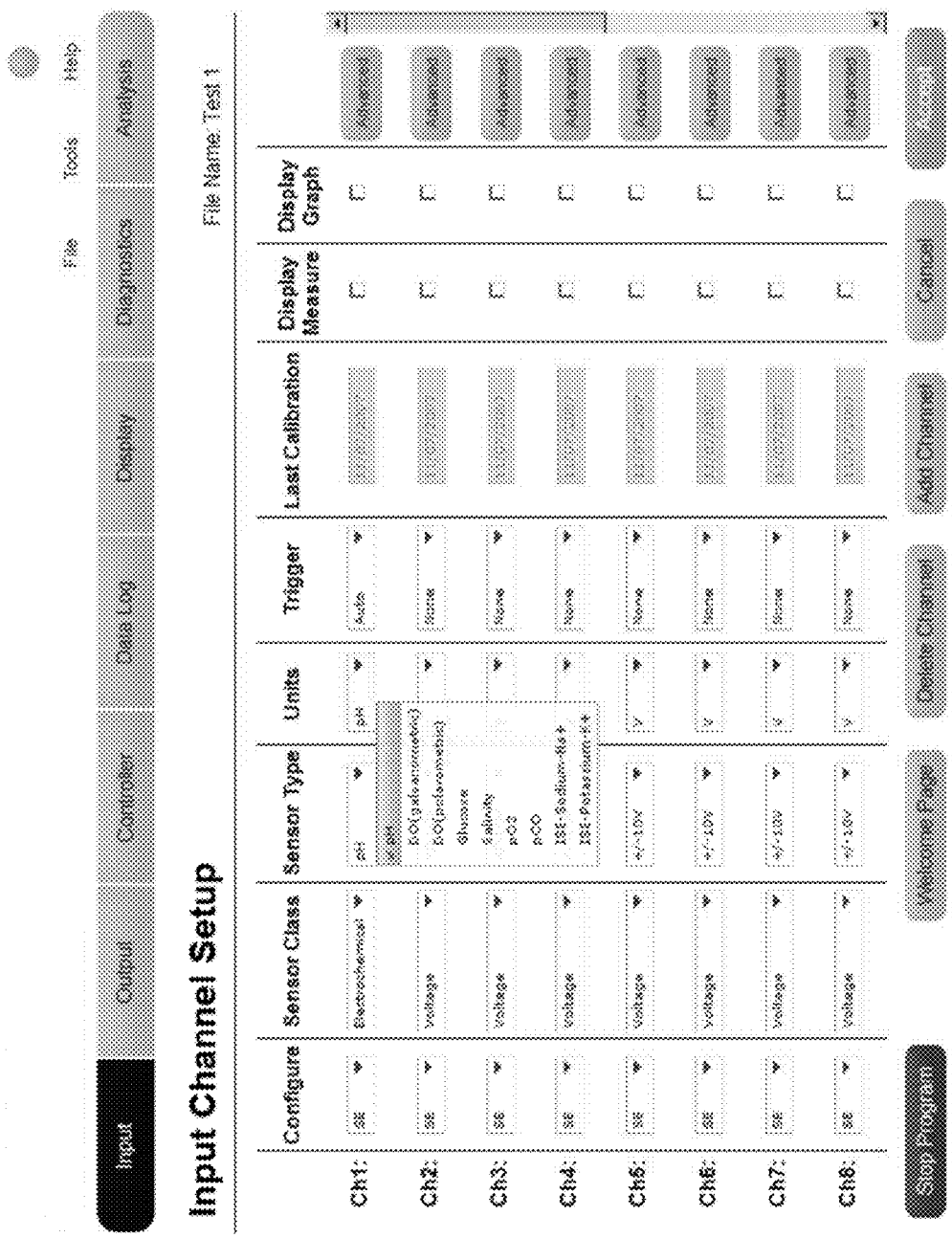
Figure 32:
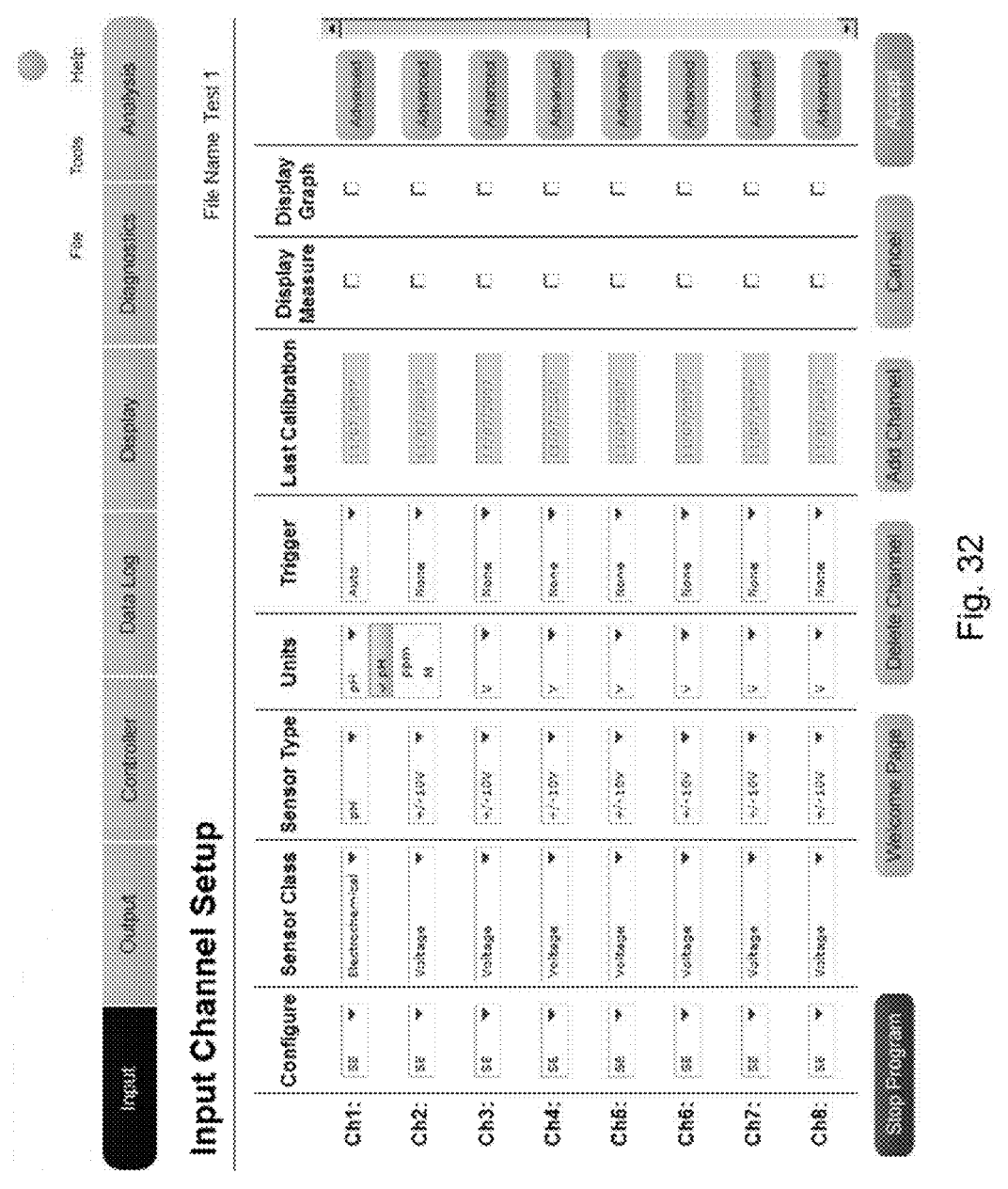
Figure 33:
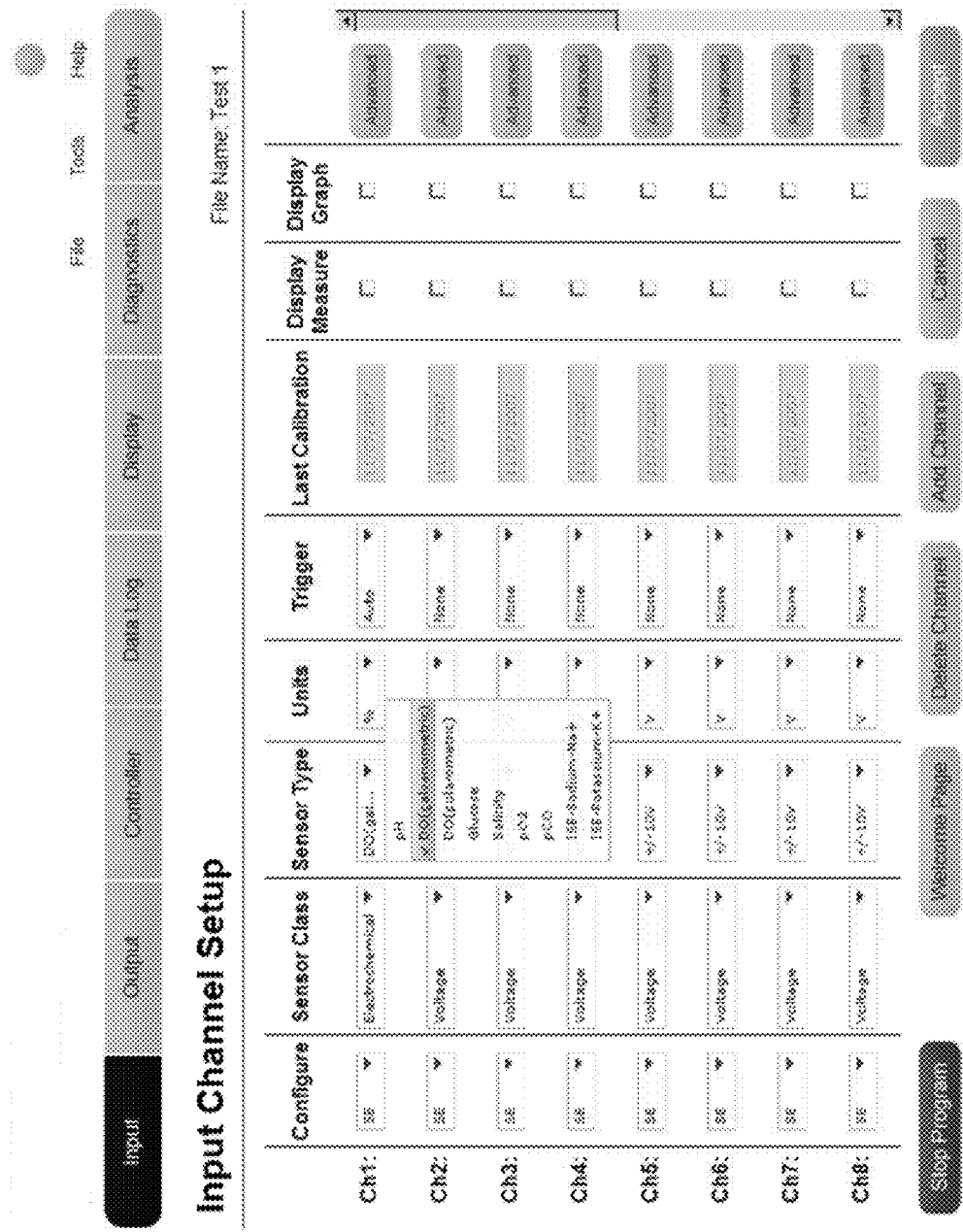
Figure 34:
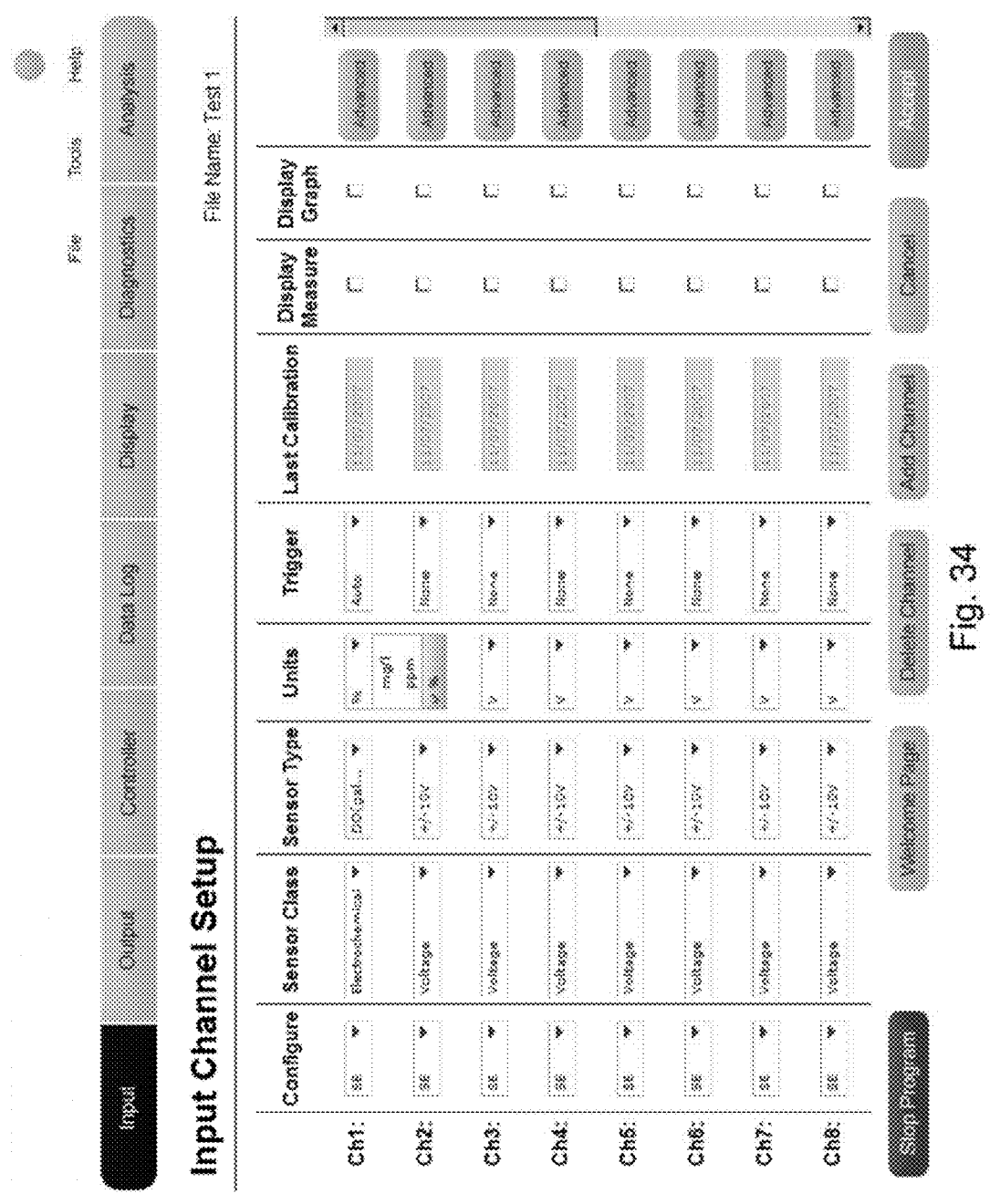

Referring to FIGS. 31-34, if the sensor class selected had been "Electrochemical" rather than "Voltage", then the sensor type drop-down menu, as shown in FIGS. 31 and 33 would no longer have voltage ranges, but instead would list various types of electrochemical sensors such as galvanometric, glucose, salinity, etc. Upon selection of one of those sensor types, for example pH or galvanometric, the units, illustrated in FIGS. 32 and 34 will correspondingly change in their respective drop-down menus, enabling the user to simply select the appropriate and preferred units for this input channel selection. Other selections result in different menus creating in effect a tree structure to be navigated, with a mouse for example, through the matrix of drop-down menus available in the input channel setup.

Figure 18:
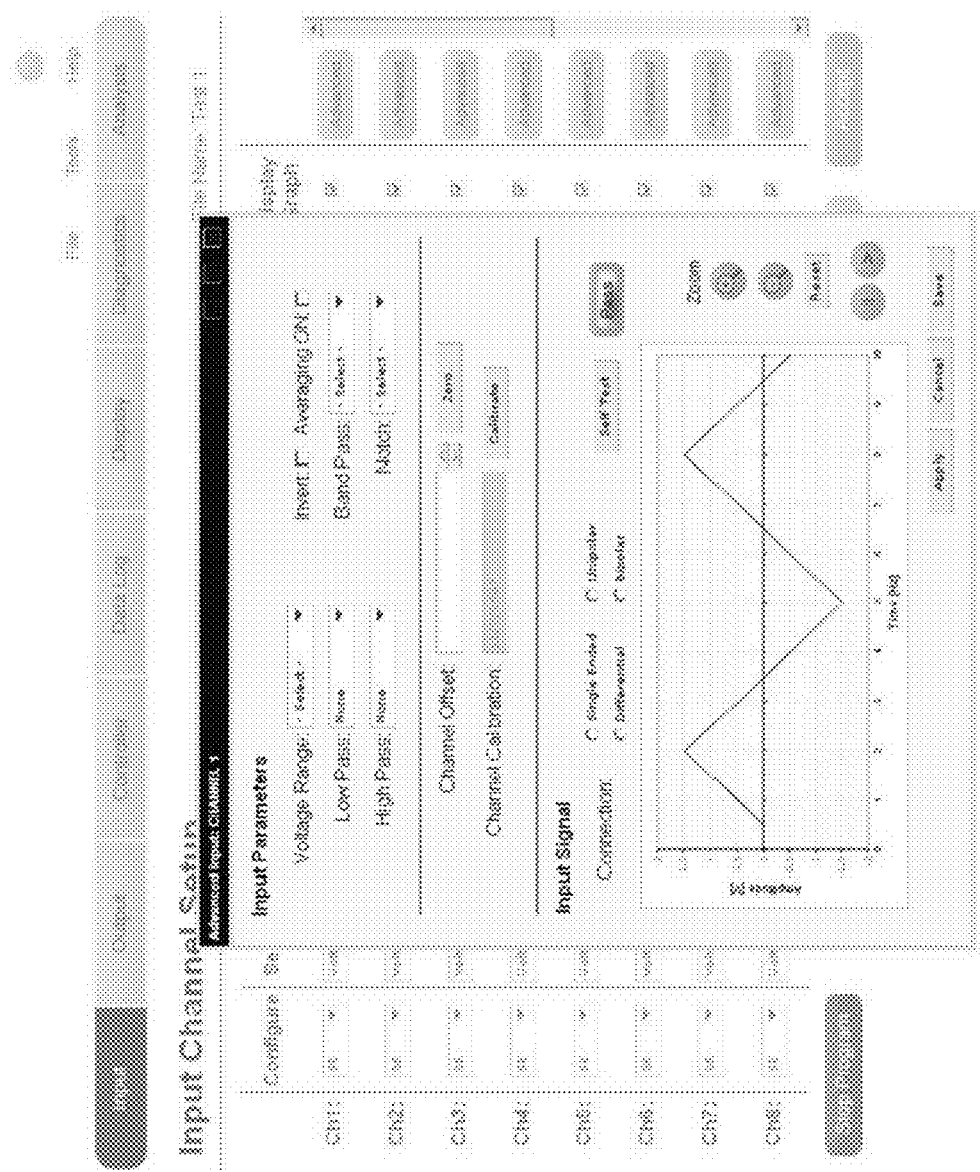
Figure 19:
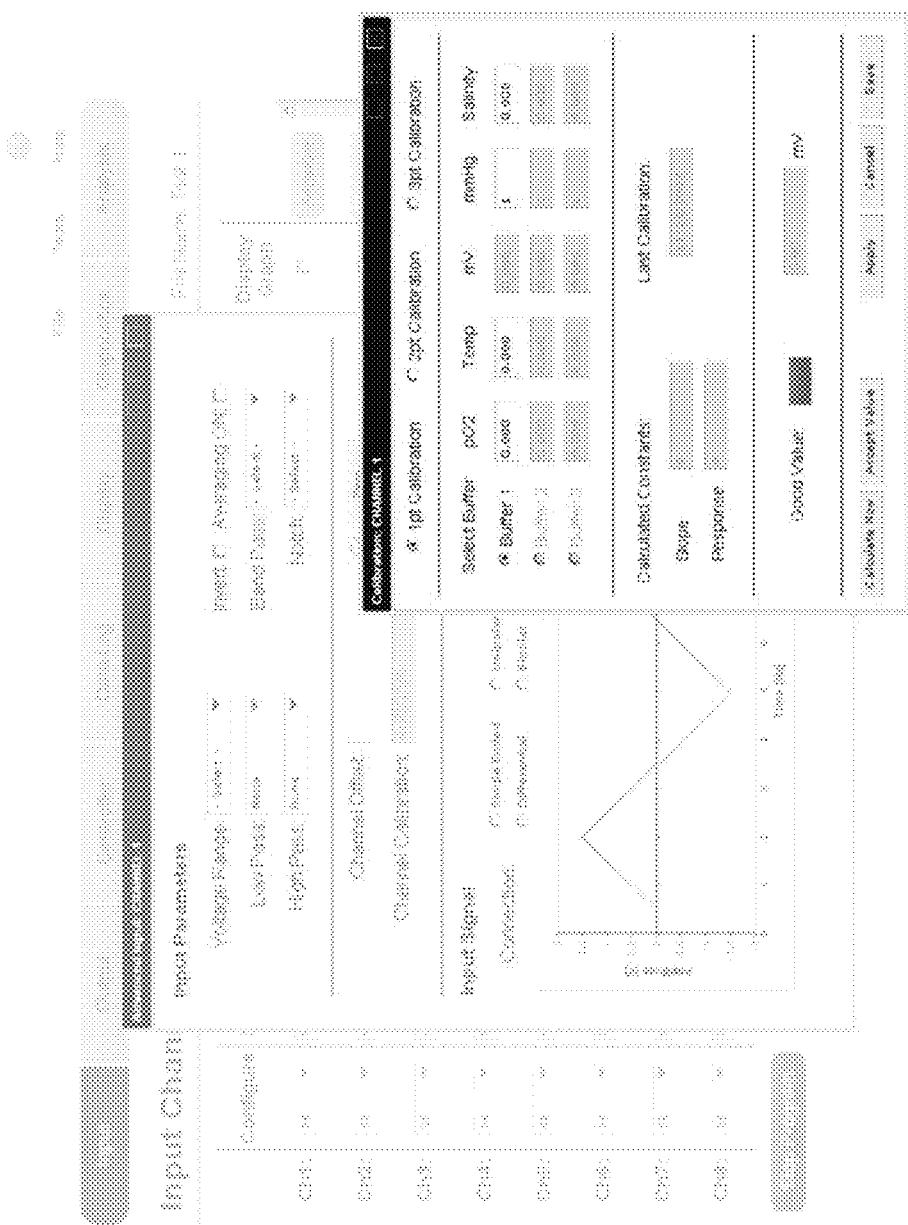

Referring to FIG. 18, in an advanced input mode, each channel can be used to enable data logging, to set up filtering, or to calibrate a particular input channel. This advanced setup option also allows a self test of that particular channel. The appropriate software "buttons" are illustrated in the figure. In FIG. 19, a calibration window becomes available with one point calibration being illustrated. The user can choose other calibration modes and can feed all buffer values to calibrate the channel. For example, in a 2-point Dissolved Oxygen calibration the user will fill in the numbers for 0% solution and 100% solution in buffer 1 and buffer 2 and hit Accept Value. The Calibration Constants will then be calculated and the calibration process is complete when the Apply tab is hit.

Figure 20:
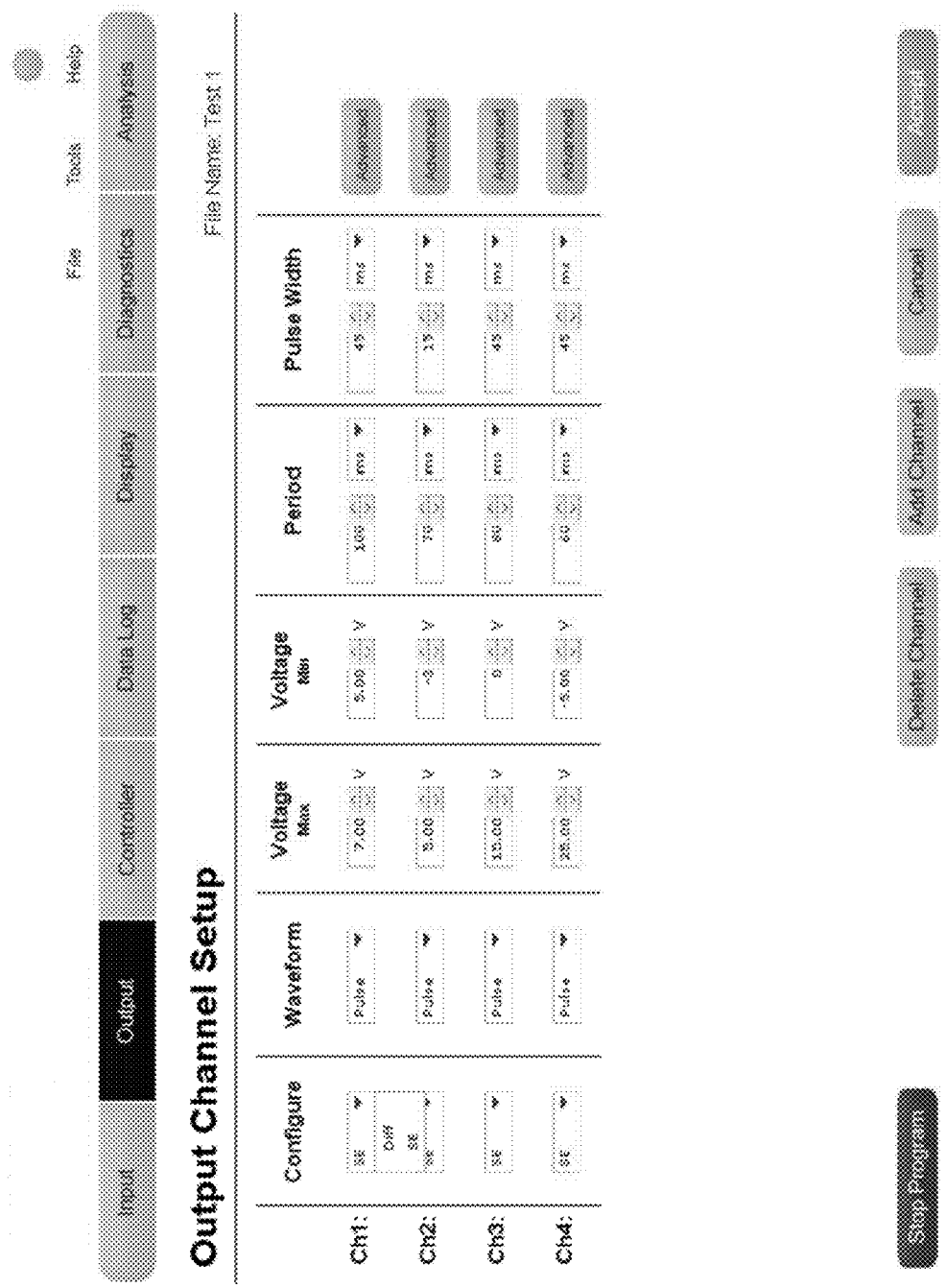
Figure 21:
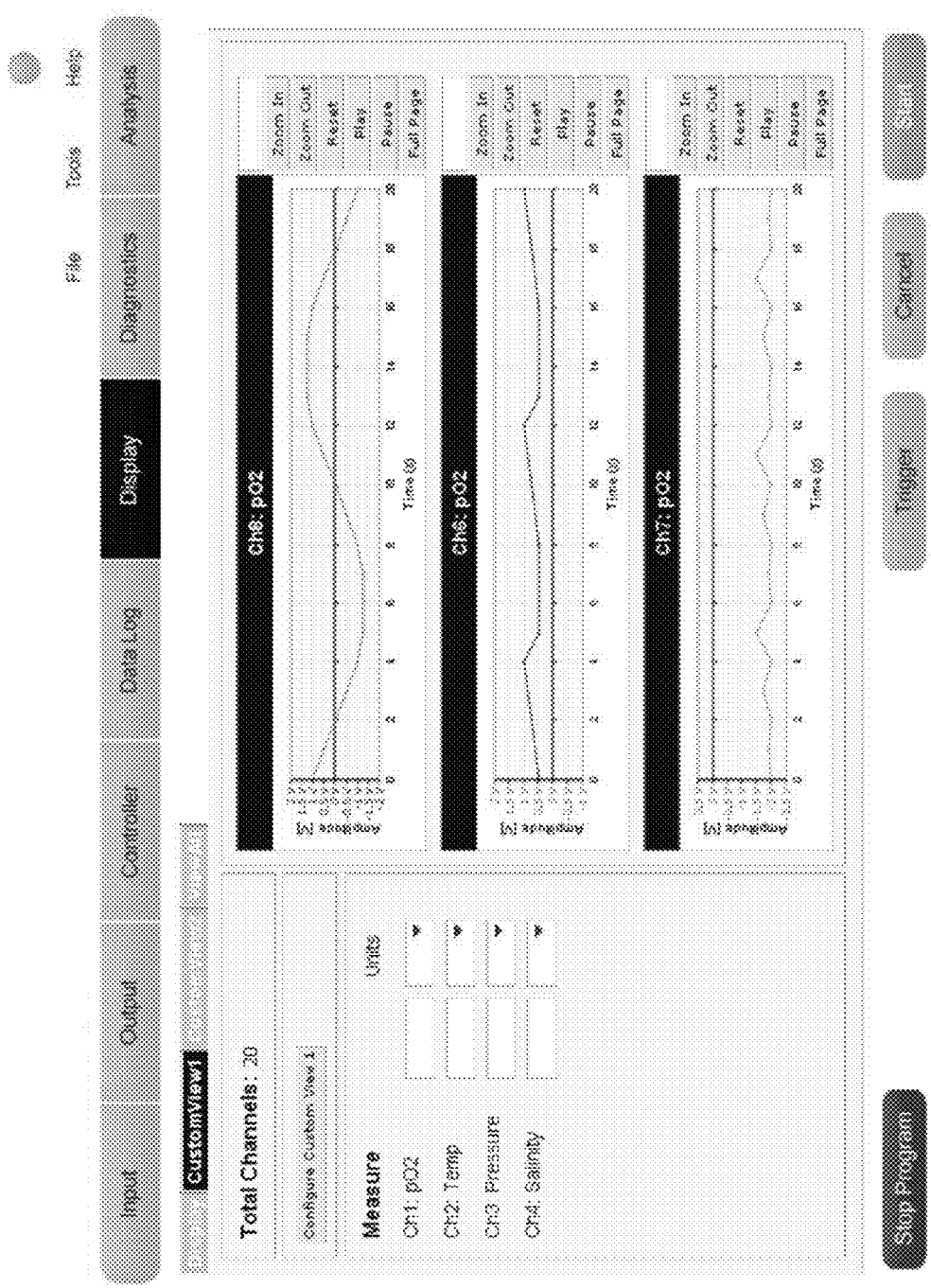
Figure 22:
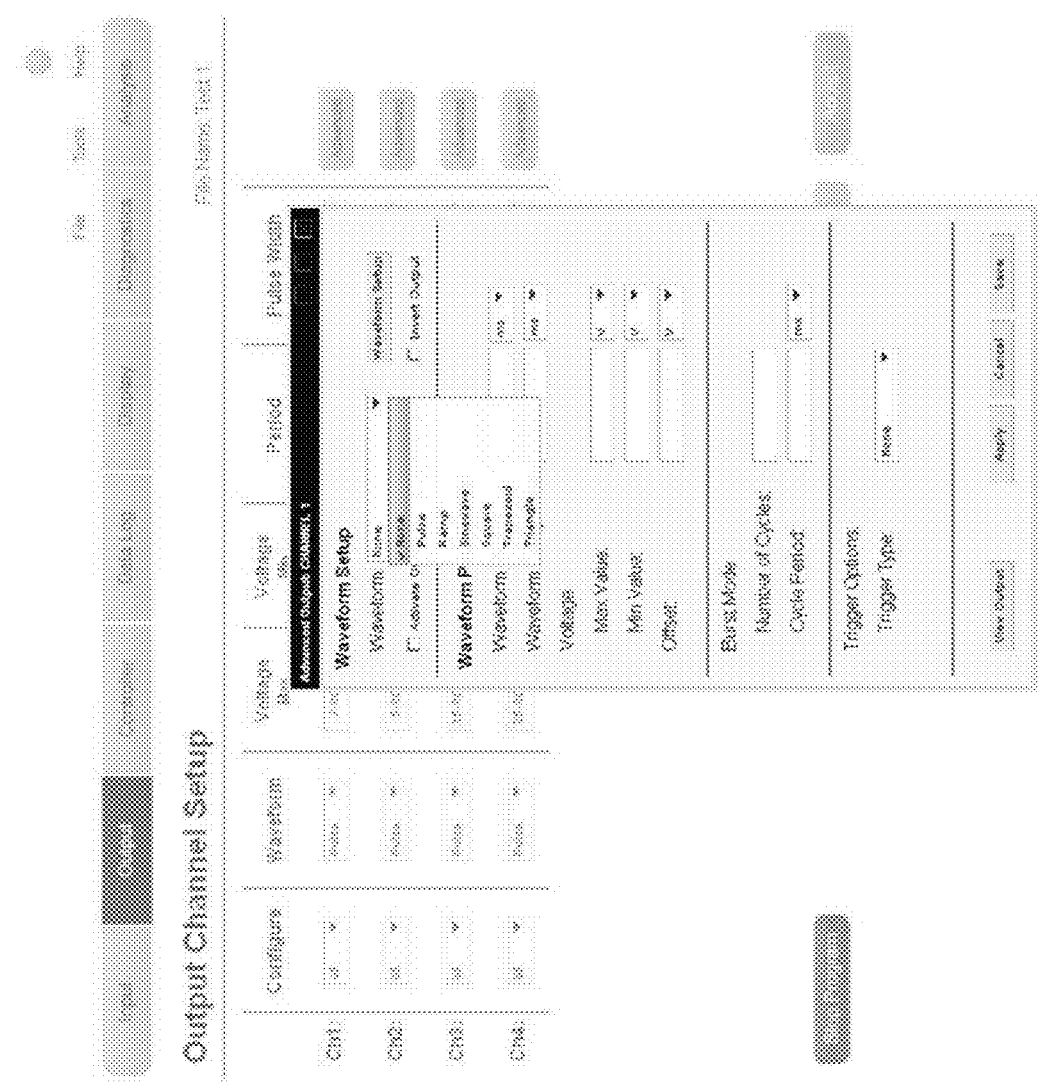
Figure 23:
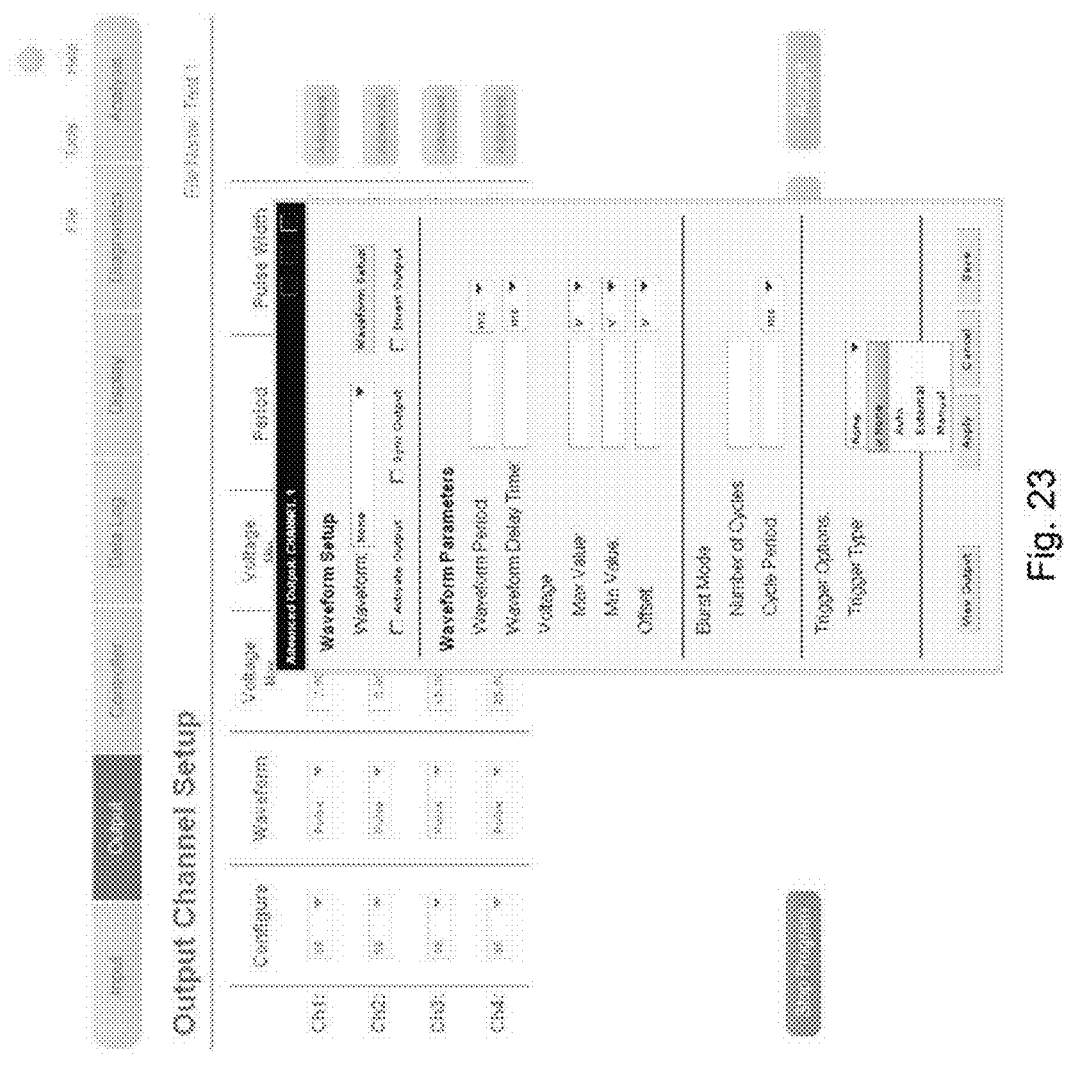
Figure 24:
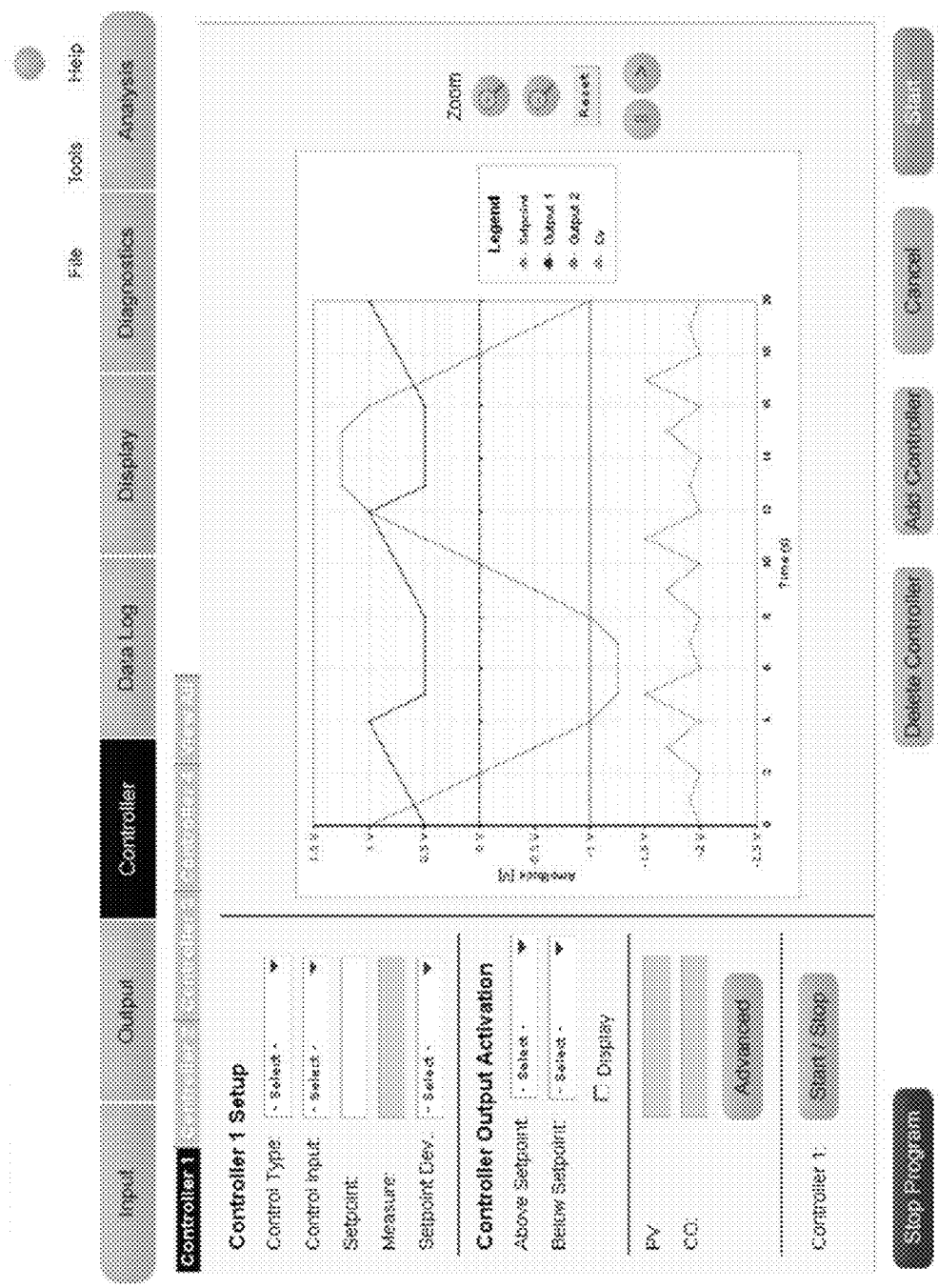
Figure 25:
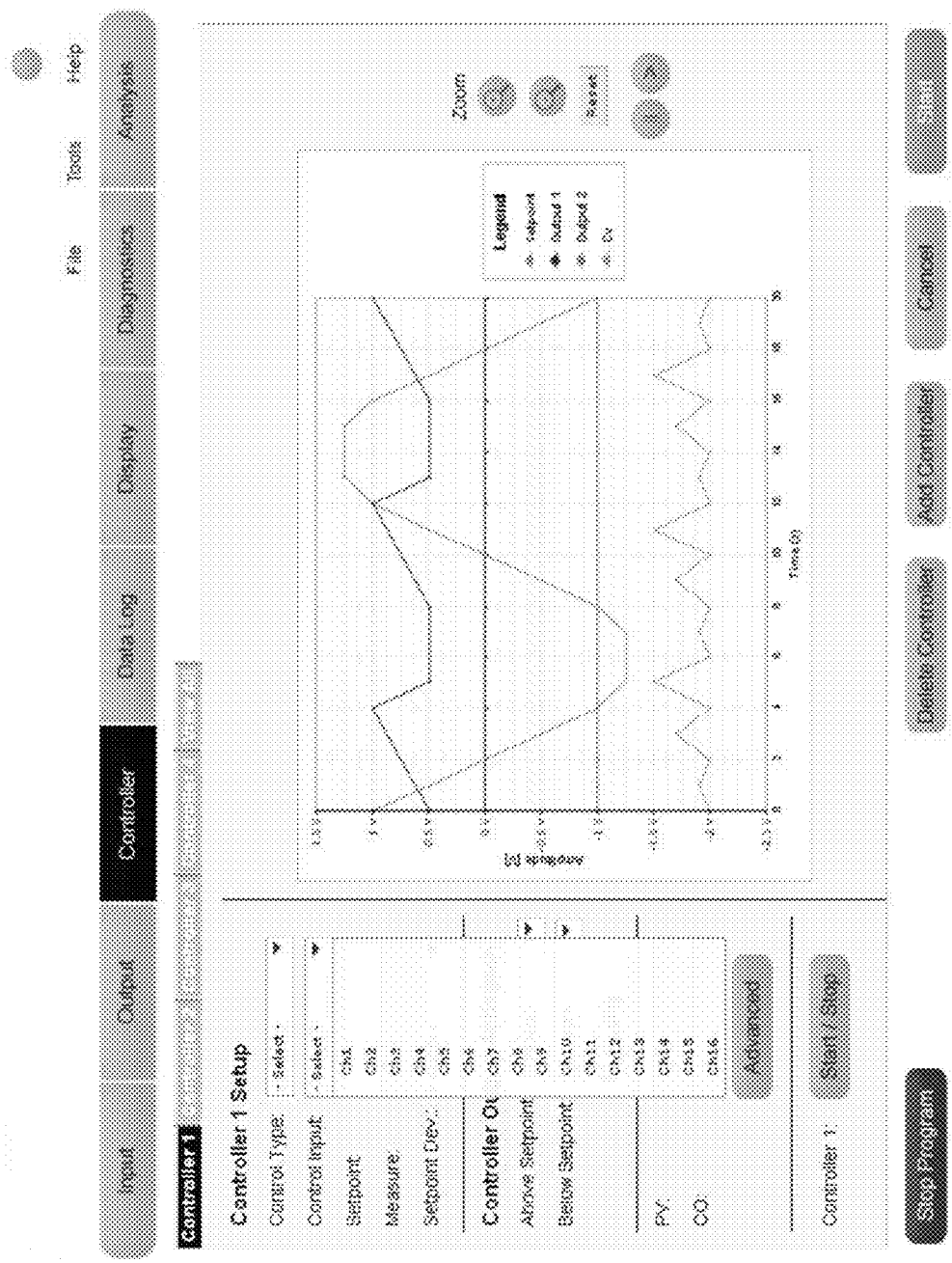

Referring to FIG. 20, the options available to set up each output channel are shown. This screen is reached by pressing the output button highlighted in FIG. 20. As with the input channels, each channel can have either a differential output or a single ended output. This choice is shown in FIG. 20. Once that choice is made, and referring to FIG. 21, the other parameters are set. In FIG. 21, for each channel, under the heading "waveform", a drop down window provides various options for the output signal waveform. Similarly, referring to FIG. 22, an advanced output drop down menu is provided for identifying, in more detail, the various waveform parameters including, for example, waveform period, delay time, minimum and maximum voltages, voltage offset, the number of cycles in the burst mode and the cycle period, and the various trigger options as illustrated in FIG. 23. Referring now to FIG. 24, all of the controller parameters are set using the control buttons available as illustrated in FIG. 24. Multiple controllers can be added or deleted using the "add controller" and "delete controller" tabs (at the bottom of FIG. 24). The "start" tab and "stop program" tabs are used to run the programmed controller. Referring to FIG. 25, there is illustrated the capability of providing as a controller input any of the channels available to be set up. These are denominated in the controller input drop down menu.

Figure 26:
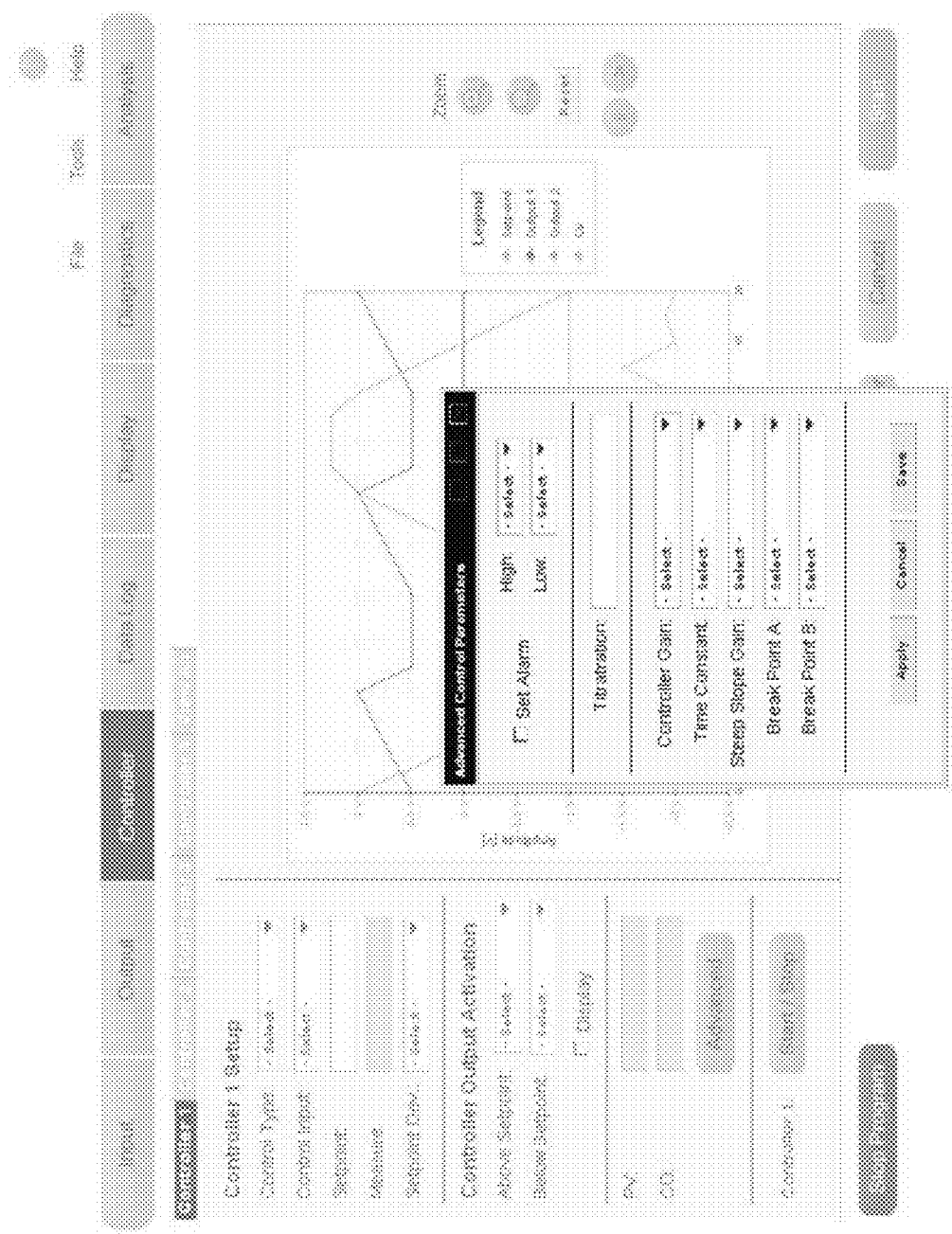

Referring to FIG. 26, the advanced controller parameter menu allows a user to set up advanced features such as controller gain, titrate details, and further allows the user to set an alarm indicator for the selected controller. Other parameters are also illustrated and able to be set as shown in the screen chart of FIG. 26.

Figure 27:
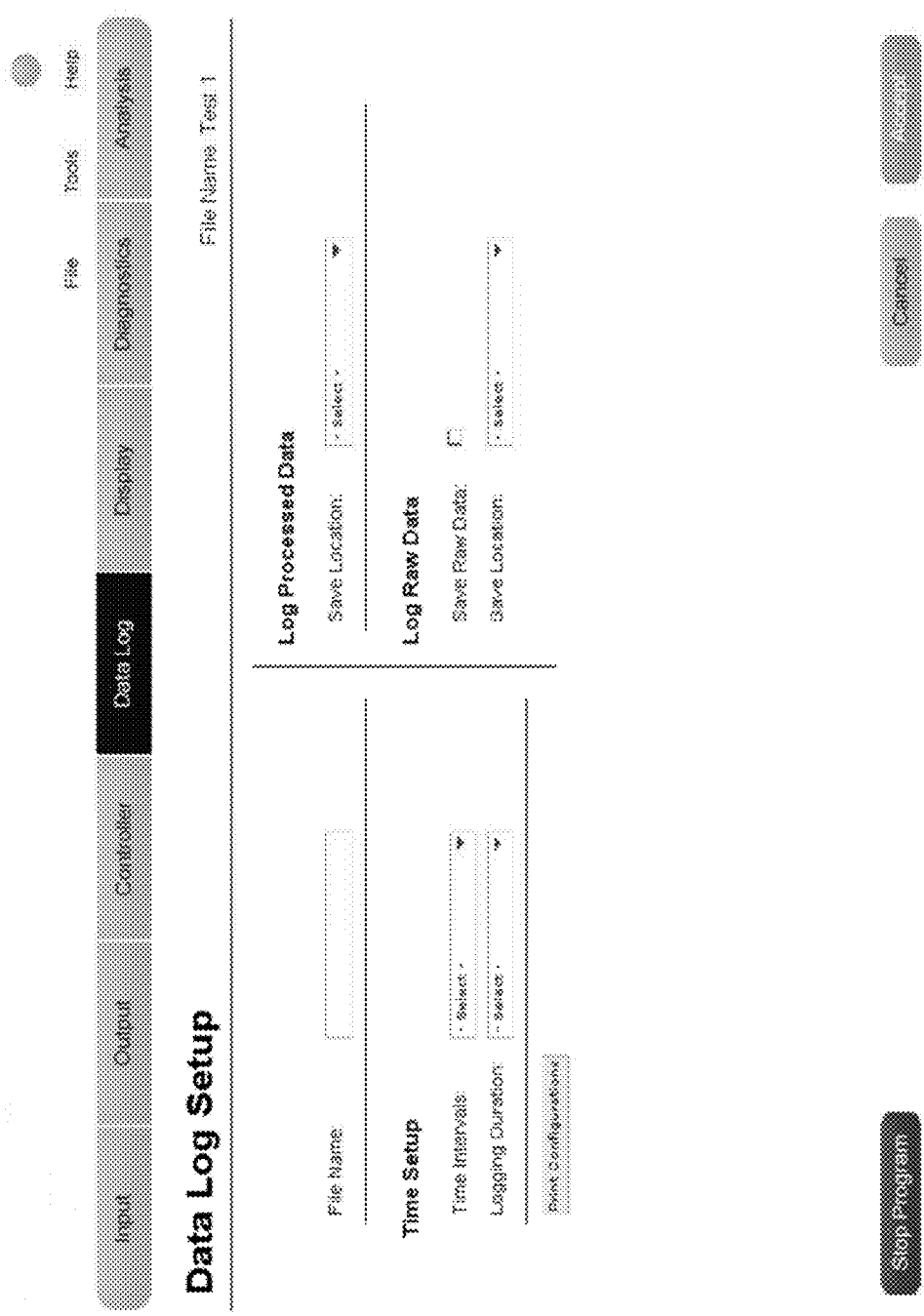

FIG. 27 allows a user to set up data logging intervals and durations. The log file can also be selected here, for example in accordance with established industry guidelines and standards and there is an option to save raw data.

Figure 28:
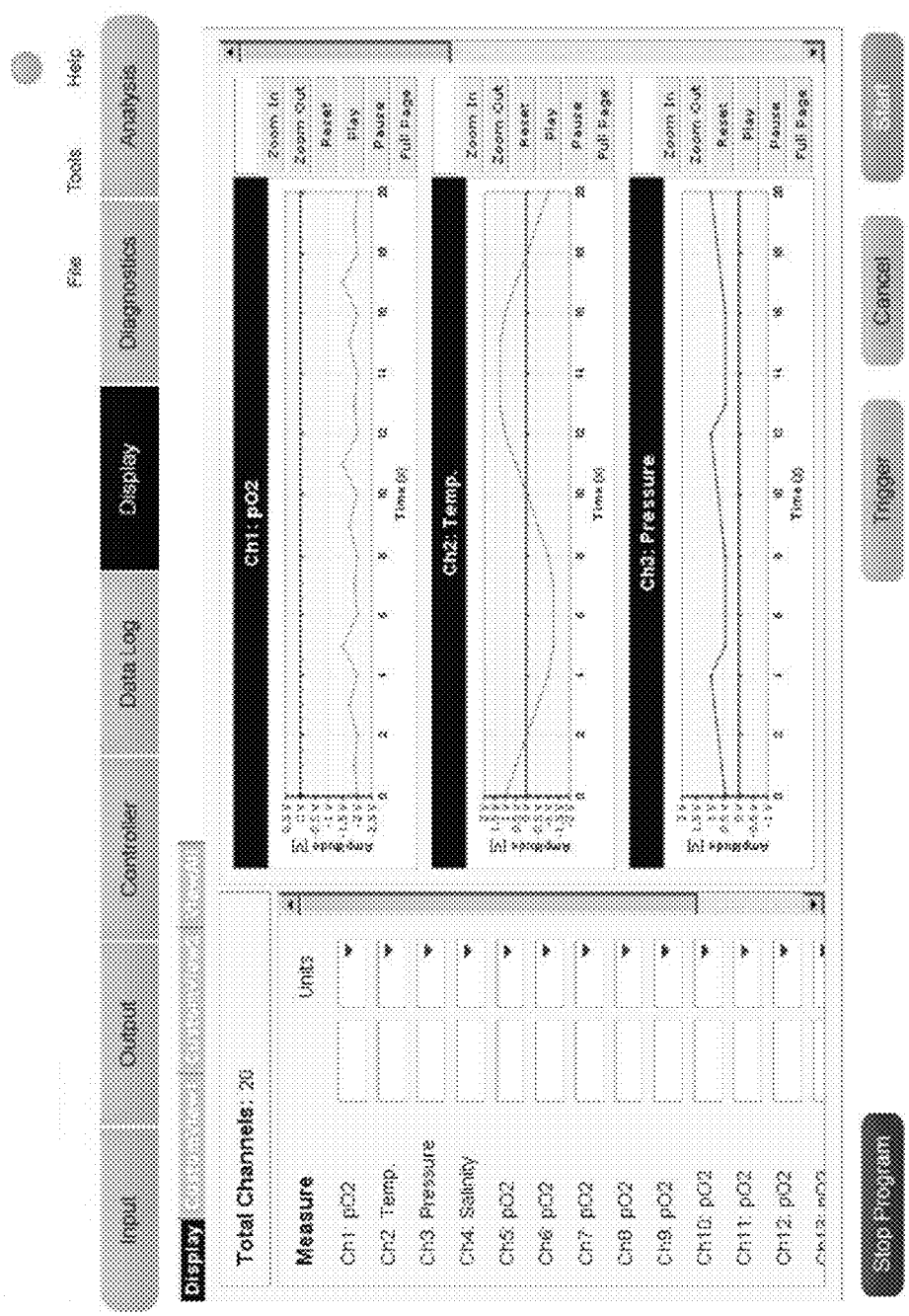

The system further, referring to FIG. 28, allows a user to view graphically as well as numerically, the data. The channels which are currently displayed graphically and/or numerically are selected using the input channel setup page, and can be displayed as illustrated in FIG. 28. The display has various desirable features such as zoom, reset, play and pause, and the display can be expanded to a full page display.

Figure 29:
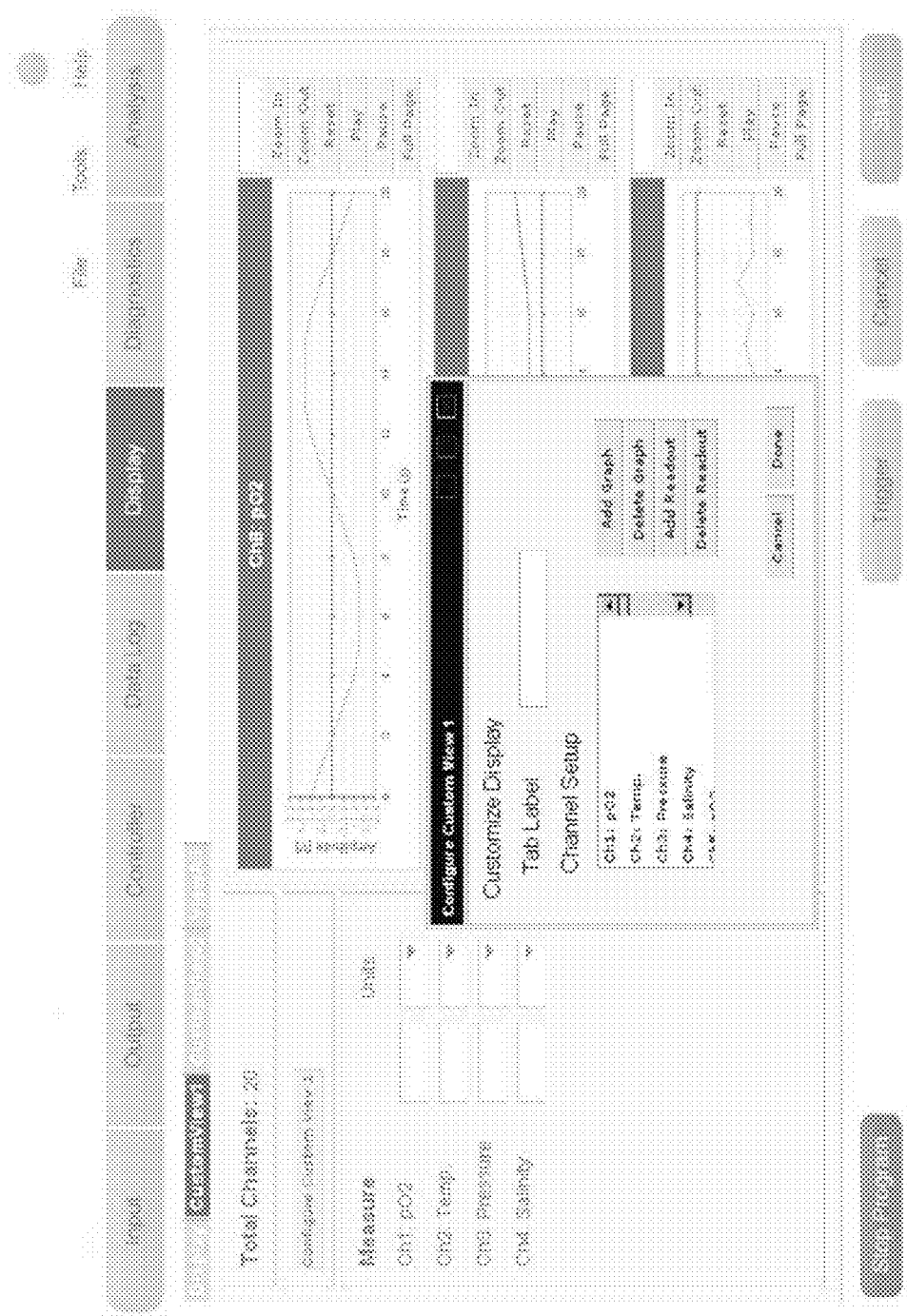

Referring now to FIG. 29, a custom view allows the user to pick and choose what is to be seen on screen. An example screen display is illustrated in the figure. In the custom view, all of the available channels are listed and the user can "add graphs/readout" and "delete graph/readout" to build the various custom views. In this way, channels which are unnecessary or which hide or mask other channels can be deleted or added and the resulting display effectively allows a better understanding of the signals input and output to and from the devices.

Figure 30:
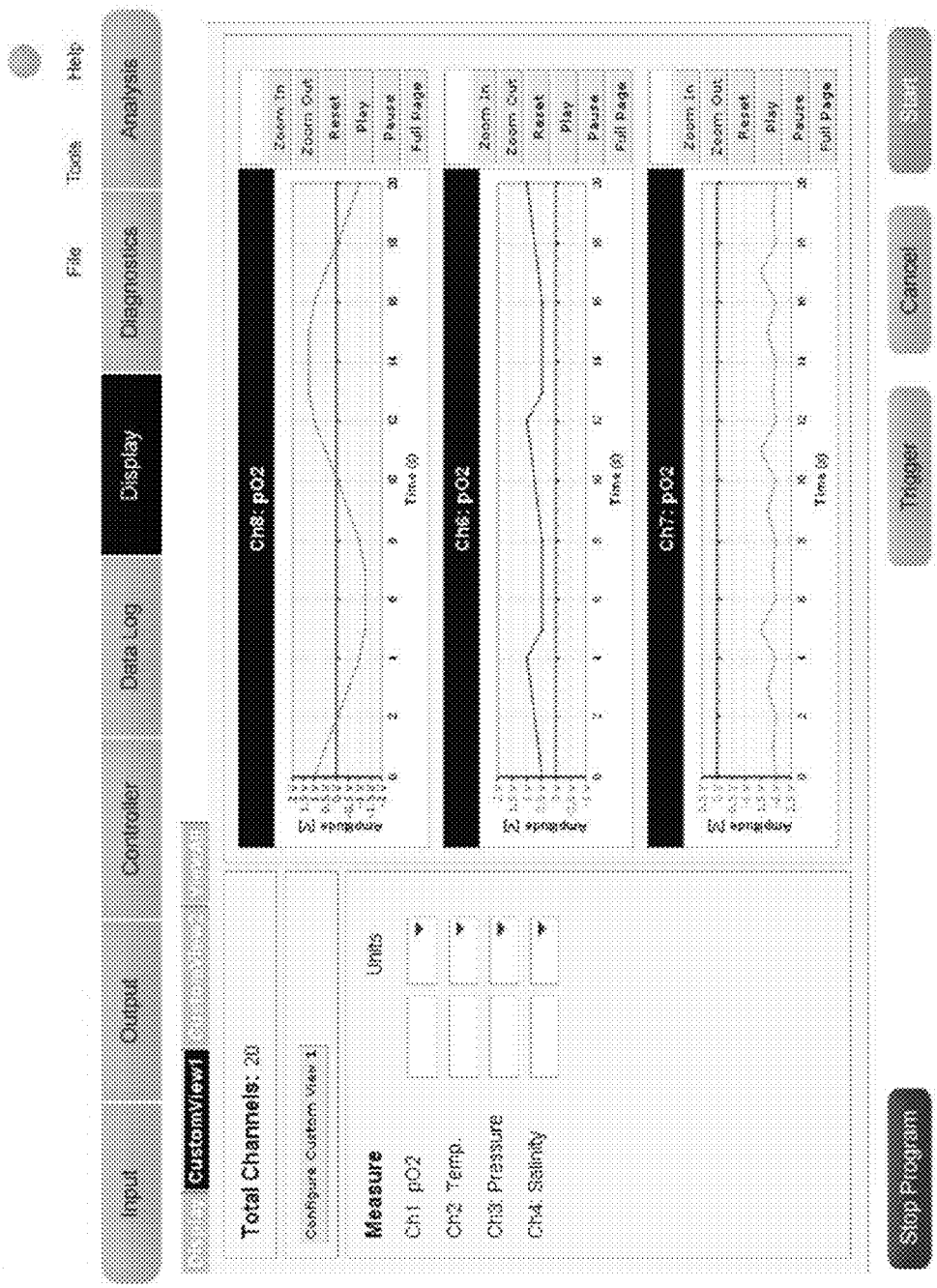

Referring to FIG. 30, the custom views of channels 8, 6, and 7 are illustrated as custom view 1.

While some of the features of the graphical user interface have been described, clearly the illustrated screenshots provide for many other features not specifically discussed. The graphical user interface provides, therefore, substantial flexibility in creating the environment needed by the system and to flexibly change the system in various connective and analytical/diagnostic ways. The graphical user interface can thus be used to either permanently configure, for example, a system on a chip or an analytical instrument, a research instrument or other device by using simple, non-technical approaches without having to understand the underlying intricacies of how one actually makes the connection, or implements in software the necessary processing required to read signals on input channels and provide output channels as described hereinabove. Further, this system, which transforms the user's simple commands into a complex arrangement of control signals, is neither specifically limited to the biosensor environment in which it is described, nor is it limited to the specific parameters which are illustrated and/or discussed herein.

As a result, the structure and system described hereinabove enables a flexible system on a chip to be produced using both analog and digital elements in a side-by-side relationship on a single chip (or if required two or more chips, for example an analog chip and a connected digital chip) to allow both hardwired burning of connections as well as programmed connections to be made, and thus enable a single multi-layer chip structure or a multi-chip module to be easily modified for many purposes. Those purposes include various purposes described in U.S. Pat. Nos. 6,029,090 and 6,684,106 as well as all the other Herbst issued U.S. Pat. Nos. 6,021,347, 6,708, 066, 7,526,334, 7,517,311, 7,937,683, and 7,160,241, U.S. pending patent application Ser. Nos. 11/063,195, 11/151,967, 11/213,050, 12/098,257, 12/431,730, 12/485,855, 12/507, 506, and 13/085,366, and International Publication No. WO 2010/065678 A1. While these relate substantially to the medical application field, that is not the only use of such a system on a chip which can be adapted for uses beyond medical applications, including, for example, a wide-range of measurement and control systems.

Other features and advantages of the invention will be apparent to those practiced within the field, and are within the scope of the following claims.

What is claimed is:

1. A user configurable instrument comprising:
 a plurality of analog elements;
 a plurality of digital elements;
 a plurality of connection elements between the plurality of analog elements and the plurality of digital elements, wherein a first portion of the plurality of analog elements and the plurality of digital elements receives inputs from one or more sources and wherein a second portion of the plurality of analog elements and the plurality of digital elements generates at least one of output signals for generating control signals and outputs presenting one or more measurements to one or more output receiving elements based on the received inputs; arid
 a configurable graphical user interface system that includes at least one of a processor and a programmable logic device to interface with:
  a user tree structure that receives one or more input or output functions of the user configurable instrument on one or more graphical user interfaces; and
  a hidden tree structure that configures at least one of: the plurality of analog elements, the plurality of digital elements, and the plurality of connection elements by connecting elements and defining operating characteristics in response to the one or more functions of the user configurable instrument selected on the one or more graphical user interfaces.

2. The user configurable instrument of claim 1, wherein the desired functions include at least one of: a desired input, a desired output, a desired output signal, and a desired feedback.

3. The user configurable instrument of claim 1, further comprising a communications interface module for receiving and sending wireless communications.

4. The user configurable instrument of claim 1, wherein the user tree structure of the configurable graphical user interface system provides the desired functions for selection by at least one of: sensor class, sensor functionality, and sensor characteristics.

5. The user configurable instrument of claim 1, wherein the user tree structure of the configurable graphical user interface system allows the user to simultaneously configure a plurality of measurements on a plurality of channels, wherein the plurality of measurements are at least one of: identical measurements, different measurements, measurements of a similar type, and synchronized measurements.

6. The user configurable instrument of claim 1, wherein the user tree structure of the configurable graphical user interface system defines measurements for at least one of $pO_2$, pH, various ions, temperature, blood gases, bodily electrical signals, and biomarkers.

7. The user configurable instrument, of claim 1, wherein the hidden tree structure of the configurable graphical user interface system configures the user configurable instrument in response to receiving at least one of sensor inputs and user control signals.

8. The user configurable instrument of claim 1, wherein the configurable graphical user interface system includes an embedded web server.

9. The user configurable instrument of claim 1, wherein the graphical user interface system is an input system for at least one of diagnostic system and a treatment system.

10. The user configurable instrument of claim 1, wherein the one or more sources provide digitized data.

11. A configurable chip module system that includes:
 a plurality of analog elements;
 a plurality of digital elements; and
 a plurality of connection elements between the plurality of analog elements and the plurality of digital elements, wherein a first portion of the plurality of analog elements and the plurality of digital elements receives inputs from one or more sources and wherein a second portion of the plurality of analog elements and the plurality of digital elements generates at least one of output signals for generating control signals and outputs presenting one or more measurements to one or more output receiving elements based on the received inputs; and
 a configurable graphical user interface system that includes at least one of a processor and a programmable logic device to interface with:
  a user tree structure that receives one or more input or output functions of the user configurable instrument on one or more graphical user interfaces; and
  a hidden tree structure that configures at least one of: the plurality of analog elements, the plurality of digital elements, and the plurality of connection elements by connecting elements and defining operating characteristics response to the one or more functions of the user configurable instrument selected on the one or more graphical user interfaces.

12. The configurable chip module system of claim 11, wherein the desired functions include at least one of: a desired input, a desired output, a desired output signal, and a desired feedback.

13. The configurable chip module system of claim 11, further comprising a communications interface module for receiving and sending wireless communications.

14. The configurable chip module system of claim 12, wherein the user tree structure of the configurable graphical user interface system provides the desired functions for selection by at least one of: sensor class, sensor functionality, and sensor characteristics.

15. The configurable chip module system of claim 12, wherein the user tree structure of the configurable graphical user interface system allows the user to simultaneously configure a plurality of measurements on a plurality of channels, wherein the plurality of measurements are at least one of: identical measurements, different measurements, measurements of a similar type, and synchronized measurements.

16. The configurable chip module system of claim 11, wherein the user tree structure of the configurable graphical user interface system defines measurements for at least one of $pO_2$, pH, various ions, temperature, blood gases, bodily electrical signals, and biomarkers.

17. The configurable chip module system of claim 11, wherein the hidden tree structure of the configurable graphical user interface system configures the configurable chip module system in response to receiving at least one of sensor inputs and user control signals.

18. The configurable chip module system of claim 11, wherein the graphical user interface system is an input system for at least one of a diagnostic system and a treatment system.

19. The configurable chip module system of claim 11, wherein the one or more sources provide digitized data.

20. A configurable chip module system comprising:
a plurality of analog elements;
a plurality of digital elements;
a plurality of connection elements between the plurality of analog elements and the plurality of digital elements, wherein a first portion of the plurality of analog elements and the plurality of digital elements receives inputs from one or more sources and wherein a second portion of the plurality of analog elements and the plurality of digital elements generates at least one of output signals for generating control signals and outputs presenting one or more measurements to one or more output receiving elements based on the received inputs; and
a configuration system that includes at least one of a processor and a programmable logic device to interface with a user tree structure and a hidden tree structure, wherein the user tree structure provides one or more graphical user interfaces that receive selections entered by a user to modify a structure of the chip module system and wherein the hidden tree structure configures the plurality of connection elements by connecting elements and defining operating characteristics in response to receiving the selections entered on the one or more graphical user interfaces.

21. The configurable chip module system of claim 20, wherein the configurable chip module system comprises a plurality of predetermined mask layers and a plurality of custom configurable mask layers, wherein the user configures desirable functions in the plurality of custom configurable mask layers.

22. The configurable chip module system of claim 21, wherein the plurality of custom configurable mask layers are laid adjacent to a flexible, predefined, functional structure.

23. The configurable chip module system of claim 20, wherein the selections include at least one of: a desired input, a desired output, a desired output signal, and a desired feedback.

24. The configurable chip module system of claim 20, wherein the configurable chip module system is configured to measure a plurality of parameters using, one or more of the plurality of analog elements and the plurality of digital elements.

25. The configurable chip module system of claim 20, wherein the configurable chip module system is configured to organize the plurality of analog elements and the plurality of digital elements by at least one of sensor functionality and sensor characteristics.

26. The configurable chip module system of claim 20, wherein the chip module system comprises a plurality of layers that are organized by functionality and wherein the user, prior to manufacture, selects one or more of the plurality of layers for including in the chip module system.

27. The configurable chip module system of claim 20, wherein the chip module system allows the user to select the one or more of the plurality of layers by selecting desired chip functions of the chip module system.

28. The configurable chip module system of claim 20, wherein the graphical user interface system is an input system for at least one of a diagnostic system and a treatment system.

29. The configurable chip module system of claim 20, wherein the one or more sources provide digitized data.

* * * * *

UNITED STATES PATENT AND TRADEMARK OFFICE
CERTIFICATE OF CORRECTION

PATENT NO. : 8,595,672 B2
APPLICATION NO. : 13/152242
DATED : November 26, 2013
INVENTOR(S) : Ewa Herbst It is certified that error appears in the above-identified patent and that said Letters Patent is hereby corrected as shown below:

In the Claims

Column 11, line 50, "inputs; arid," should be --inputs; and--.
Column 12, line 32, "of diagnostic," should be --of a diagnostic--.

Signed and Sealed this
Twelfth Day of August, 2014

Michelle K. Lee
*Deputy Director of the United States Patent and Trademark Office*